US012667555B2

(12) United States Patent
Lim et al.

(10) Patent No.: US 12,667,555 B2
(45) Date of Patent: Jun. 30, 2026

(54) TREATMENT OF OVARIAN CANCER WITH NIROGACESTAT

(71) Applicant: SpringWorks Therapeutics, Inc., Stamford, CT (US)

(72) Inventors: Allison Lim, Stamford, CT (US); Shinta Cheng, Stamford, CT (US); Todd Webster Shearer, Stamford, CT (US); Rex Williams, Stamford, CT (US); Kristin Patterson, Stamford, CT (US)

(73) Assignee: SPRINGWORKS THERAPEUTICS, INC., Stamford, CT (US)

( * ) Notice: Subject to any disclaimer, the term of this patent is extended or adjusted under 35 U.S.C. 154(b) by 206 days.

(21) Appl. No.: 18/440,869

(22) Filed: Feb. 13, 2024

(65) Prior Publication Data

US 2024/0180874 A1 Jun. 6, 2024

Related U.S. Application Data

(63) Continuation of application No. 18/543,022, filed on Dec. 18, 2023, now Pat. No. 12,036,207, which is a continuation-in-part of application No. 18/491,525, filed on Oct. 20, 2023, now Pat. No. 11,951,096, which is a continuation-in-part of application No. 18/320,547, filed on May 19, 2023, now Pat. No. 11,872,211.

(60) Provisional application No. 63/365,193, filed on May 23, 2022, provisional application No. 63/365,125, filed on May 20, 2022.

(51) Int. Cl.
*A61K 31/417* (2006.01)
*A61K 9/00* (2006.01)

(52) U.S. Cl.
CPC .......... *A61K 31/417* (2013.01); *A61K 9/0053* (2013.01)

(58) Field of Classification Search
None
See application file for complete search history.

(56) References Cited

U.S. PATENT DOCUMENTS

| | | | |
|---|---|---|---|
| 7,465,800 | B2 | 12/2008 | Jaworsky et al. |
| 7,795,447 | B2 | 9/2010 | Brodney et al. |
| 8,399,469 | B2 | 3/2013 | Bando et al. |
| 10,590,087 | B1 | 3/2020 | Greer et al. |
| 10,941,118 | B2 | 3/2021 | Greer et al. |
| 11,872,211 | B2 | 1/2024 | Lim et al. |
| 2005/0215610 | A1 | 9/2005 | Brodney et al. |
| 2019/0185559 | A1 | 6/2019 | Russell et al. |
| 2021/0040045 | A1 | 2/2021 | Greer et al. |

FOREIGN PATENT DOCUMENTS

| | | | | |
|---|---|---|---|---|
| CA | 2991096 | A1 | 1/2017 | |
| CN | 112843238 | A * | 5/2021 | ............ A61K 45/06 |
| WO | 2005092864 | A1 | 10/2005 | |
| WO | 2014191894 | A1 | 12/2014 | |
| WO | 2015092614 | A1 | 6/2015 | |
| WO | 2015171003 | A1 | 11/2015 | |
| WO | 2016046530 | A1 | 3/2016 | |
| WO | 2016198374 | A1 | 12/2016 | |
| WO | 2018045273 | A2 | 3/2018 | |
| WO | 2019053727 | A1 | 3/2019 | |
| WO | 2020208572 | A1 | 10/2020 | |
| WO | 2021146604 | A1 | 7/2021 | |
| WO | 2021183934 | A1 | 9/2021 | |
| WO | 2021195362 | A1 | 9/2021 | |
| WO | 2023049694 | A1 | 3/2023 | |
| WO | 2023064872 | A1 | 4/2023 | |
| WO | 2023081830 | A2 | 5/2023 | |

OTHER PUBLICATIONS

A Phase I Trial of PF-03084014 in Patients with Advanced Solid Tumor Malignancy and T-cell Lymphoblastic Leukemia/ Lymphoblastic Lymphoma. ClinicalTrials.gov ID:NCT00878189. (Study Concluded Nov. 22, 2016). (Year: 2016).
"A Randomized, Double-Blind, Placebo-Controlled, Phase 3 Trial of Nirogacestat Versus Placebo in Adult Patients With Progressing Desmoid Tumor/ Aggressive Fibromatosis (DT /AF)", Protocol NIR-DT-301, Dec. 2018, 7 pages.
"CAS Scifinder Nirogacestat—Predicted Solubility", American Chemical Society (ACS); (CAS registry No. 1290543-63-3) accessed online 2023:1-5.
NIH-NCI, "Common terminology criteria for adverse events", v. 5.0, 2017, p. 1-146.
Altman, Ben, et al., The Desmoid Tumor Working Group, "The management of desmoid tumours: A joint global consensus-based guideline approach for adult and pediatric patients", European Journal of Cancer, 2020, 127:96-107 (Jan. 28, 2020).
Bauer, T.M. , "Clinical management of adverse events associated with lorlatinib", The Oncologist, 2019, 24:1103-1110.
Chi, K.N. , et al., "A phase 2 study of patupilone in patients with metastatic castration-resistant prostate cancer previously treated with docetaxel", Canadian Urologic Oncology Group study P07a, Annals of Oncology, 2012, 23:53-58.
Coyne, G.O., "Activity of PF-03084014 in adults with desmoid tumors/aggressive fibromatosis", J Clin Oneal 34 (2016) Poster# 11028.
Coyne, G.O., "Phase II Trial of the gamma-secretase inhibitor nirogacestat (PF-03084014) in adults with desmoid tumors/ aggressive fibramatosis", NCI Protocol # 14-C-0007; Version Date Dec. 3, 2021 NCT No. NCT01981551, 1-66.
Du Fy , et al., "Targeting cancer stem cells in drug discovery: Current state and future perspectives", World J Stem Cells. Jul. 26, 2019;11 (7):398-420. (Year: 2019).
Gounder, M , et al., "Nirogacestat, a y-Secretase Inhibitor for Desmoid Tumors", N Engl J Med 2023, 388:898-912 DOI: 10.1056/ NEJMoa2210140).
Hosea, N.A. , et al., "Predicting pharmacokinetic profiles using in silica derived parameters", Molecular Pharmaceutics, 2013, 10:1207-1215.

(Continued)

*Primary Examiner* — Brian J Davis
(74) *Attorney, Agent, or Firm* — Blank Rome LLP

(57) ABSTRACT

The present disclosure relates to improved methods of treating ovarian cancer with nirogacestat.

30 Claims, No Drawings

(56) References Cited

OTHER PUBLICATIONS

Irusta, et al., Biol Reprod. 2013, 89(1):9, doi: 10.1095/biolreprod. 113.108100.
Kasper, B , et al., "Desmoid tumors: to treat or not to treat, that is the question", Cancer, 2020, 126(24):5213-5221.
Kummar, Shivaani, et al., "Clinical Activity of the y-Secretase Inhibitor PF-03084014 in Adults with Desmoid Tumors (Aggressive Fibromatosis)", J Clin Oncology, 2017, 34(14):1561-1569.
Ma, C, "Protocol Administrative Letter", 2020, 1-87.
Merck, "A Parallel-Group, Double-Blind, Long Term Safety and Efficacy Trial of MK-8931 (SCH 900931) in Subjects with Amnestic Mild Cognitive Impairment Due to Alzheimer's Disease (Prodromal AD)", p. 1-85, 2019 © https://clinicaltrials.gov.ProvidedDocs/01/NCT01953601/Prot_SAP_000.pdf.
Messersmith , et al., "A Phase I, dose-finding study in patients with advanced solid malignancies of the oral y-secretase inhibitor PF-03084014". Clin Cancer Res. Jan. 1, 2015;21(1):60-7. (Year: 2015).
Miner, P.B. , et al., "Comparison of gastric pH with omeprazole magnesium 20.6 mg (Prilosec OTC) o.m. famotidine 10 mg, (Pepcid AC) b.d. and famotidine 20 mg b.d. over 14 days of treatment", Alimentary Pharmacology & Therapeutics, 2007, 25: 103-109.
Shah , et al., N Engl J Med. 2009, 360(26):2719-29, doi: 10. 1056/NEJMoa0902542.
X Li , et al., "The molecular mechanism of ovarian granulosa cell tumors", J Ovarian Res 11, 13 (2018) (Year: 2018).
Study Details—NIR-DT-301, Nirogacestat for Adults With Desmoid Tumor/ Aggressive Fibromatosis {DT / AF), SpringWorks Therapeutics, Inc., Dec. 2018 7 pages.
"International Search Report and written opinion issued in PCT/US2023/022881 on Oct. 5, 2023".
"International Search Report issued in PCT/US2022/079309 on Apr. 7, 2023".
"NIH-NCI Common terminology criteria for adverse events. (2022); p. 1-146".
"PUBCHEM-SID:383689933 Deposit Date: May 8, 2019 (08.05. 2019) pp. 1-6; p. 2".
Bauer, T.M. , "Clinical management of adverse events associated with lorlatinib", The oncologist 24.8 (2019): 1103-1110.
Chi, K.N. , "A phase 2 study of patupilone in patients with metastatic castration-resistant prostate cancer previously treated with docetaxel", Canadian Urologic Oncology Group study P07a. Annals of oncology 23.1 (2012): 53-58.
Coyne, G.O. , "Phase II Trial of the gamma-secretase inhibitor nirogacestat (PF-03084014) in adults with dismoid tumors/aggressive fibramatosis", NCI Protocol # 14-C-0007; Version Date Dec. 3, 2021 NCT No. NCT01981551; 1-66.
Coyne , "Phase II Trial of the -secretase Inhibitor PF-03084014 in Adults with Desmoid Tumors/Aggressive Fibromatosis 1-66", ClinicalTrials.gov. Web. Apr. 8, 2019; p. 3, Objectives, Study Design; p. 13, second paragraph and p. 19, Dose Modifications; DOI: https://classic.clinicaltrials.gov/ProvidedDocs/51 /NCT0 1981551/Prot_ SAP 000.pdf.
Grounder, M , et al., "Nirogacestat, a y-Secretase Inhibitor for Desmoid Tumors", N Engl J Med 2023, 388:898-912 DOI: 10.1056/NEJMoa2210140).
Hosea, N .A. , "Predicting pharmacokinetic profiles using in silica derived parameters", Molecular pharmaceutics 10.4 (2013): 1207-1215.
Kasper, B , "Desmoid tumors: to treat or not to treat, that is the question", Cancer 126.24 (2020): 5213-5221.
Kummar S., et al., "Clinical Activity of the Gamma-Secretase Inhibitor PF-03084014 in Adults With Desmoid Tumors (Aggressive Fibromatosis)," American Society of Journal of Clinical Oncology, May 10, 2017, vol. 35, No. 14, pp. 1561-1569 (11 Pages), DOI: 10.1200/JC0.2016.71.1994.
Curigliano G., et al., "Phase I Dose-finding Study of the Gamma Secretase Inhibitor PF-03084014 (PF-4014) in Combination with Docetaxel in Patients (pts) with Advanced Triple-negative Breast Cancer (TNBC)," Journal of Clinical Oncology, May 20, 2015, vol. 33, No. 15, Suppl. 1058, pp. 1058-1068 (1 Page).
Kaufman M.L., et al., "Transcriptional Profiling of Murine Retinas Undergoing Semi-Synchronous Cone Photoreceptor Differentiation," Developmental Biology, 2019, vol. 453, pp. 155-167.
Shang H., et al., "Targeting the Notch Pathway: A Potential Therapeutic Approach for Desmoid Tumors," Cancer, John Wiley and Sons Inc., United States, Nov. 15, 2015, vol. 121, No. 22, pp. 4088-4096.
Wei P., et al., "Evaluation of Selective Gamma-Secretase Inhibitor PF-03084014 for its Antitumor Efficacy and Gastrointestinal Safety to Guide Optimal Clinical Trial Design," Molecular Cancer Therapeutics, American Association for Cancer Research, United States, Jun. 2010, vol. 9, No. 6, pp. 1618-1628 (12 Pages).
Silverman R.B., "Lead Modification: Drug Design and Development," The Organic Chemistry of Drug Design and Drug Addiction, 2nd Edition, Elsevier, United States, 2004, pp. 29-32 (6 Pages), Hayhurst J., (Senior Publishing Editor).
Takahashi T., et al., "Safety and Efficacy of Gamma-Secretase Inhibitor Nirogacestat (PF-03084014) in Desmoid Tumor: Report of Four Pediatric/Young Adult Cases," Pediatric Blood Cancer, 2020, vol. 67: e28636, 6 Pages.

* cited by examiner

TREATMENT OF OVARIAN CANCER WITH NIROGACESTAT

The present application is a continuation-in-part of U.S. patent application Ser. No. 18/543,022, filed Dec. 18, 2023, which is a continuation-in-part of U.S. patent application Ser. No. 18/491,525, filed Oct. 20, 2023, which is a continuation-in-part of U.S. patent application Ser. No. 18/320,547, filed May 19, 2023, which claims the benefit of U.S. Provisional Application No. 63/365, 125, filed May 20, 2022 and U.S. Provisional Application No. 63/365,193, filed May 23, 2022, each of which is hereby incorporated by reference.

FIELD OF THE INVENTION

The present disclosure relates to improved methods of treating ovarian cancer with nirogacestat.

BACKGROUND (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide ("nirogacestat" or compound of Formula (I) shown below) is a gamma-secretase inhibitor which can inhibit Aβ-peptide production.

(I)

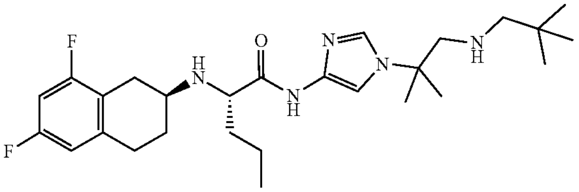

Ovarian granulosa cell tumors (OvGCTs) represent 5-7% of all ovarian cancers (approximately 1500 to 2000 newly diagnosed patients/year in the United States (US)) and are the most common subtype of ovarian sex cord tumors (70%). The average age at diagnosis for OvGCT is 50 years: 12% of OvGCT patients are younger than 30 years and 57% are between the ages of 30 and 59 years. OvGCTs are usually slow growing and often do not lead to mortality, so prevalence is high relative to incidence. Mean overall survival (OS) has been shown to be about 13 years (11-15 years) from time at diagnosis with a 10-year OS of 90%.

OvGCTs tend to recur late after primary surgery and primary platinum-based therapy. The recurrence rate in case series was 32% to 44% (longest reported time to recurrence was 40 years). Median recurrence free survival was 8.4 years (6.8-9.9 years).

OvGCTs originate from early ovarian mesenchyma and are composed of granulosa cells, thecacells, and fibroblasts.

Hyperestrogenism is reported in patients with OvGCT and is related to tumor production of estrogens, anti-Mullerian hormone (AMH), and inhibin A and B. This hormone production differentiates OvGCT from serous ovarian cancer and could serve as a tumor-specific pharmacodynamic marker.

There are currently no Food and Drug Administration (FDA) approved therapies for OvGCT. Surgery, possibly with adjuvant chemotherapy, is the mainstay of initial treatment. Adjuvant chemotherapy is typically with a platinum-based regimen: paclitaxel-carboplatin, cyclophosphamide-cisplatin, or bleomycin-etoposide-cisplatin. Objective Response Rate (ORR) from any monotherapy in the relapse setting is low. Furthermore, combination therapy in the relapse setting has failed to show an improvement in Progression Free Survival (PFS) rates. Therefore, there is an unmet need in this patient population for an agent with a higher response rate and the potential to improve PFS.

Accordingly, there is a current need for compositions comprising nirogacestat or a pharmaceutically acceptable salt thereof, to treat patients having a disease or disorder amenable to treatment with a gamma-secretase inhibitor.

SUMMARY OF THE INVENTION

The present invention includes improvement methods of treating conditions responsive to inhibition of gamma secretase, such as ovarian cancer (e.g., ovarian granulosa cell tumors), with nirogacestat and pharmaceutically acceptable salts thereof.

One embodiment is a method for treating a condition responsive to inhibition of gamma secretase, such as ovarian cancer (e.g., ovarian granulosa cell tumors), in a patient in need thereof comprising orally administering to the patient 150 mg (free base equivalent dose) of nirogacestat or a pharmaceutically acceptable salt thereof twice daily, where the method comprises one or more of:

(a) upon the patient having Grade 3 or 4 diarrhea persisting for at least 3 days despite maximal medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily;

(b) upon the patient having Grade 3 or 4 hypophosphatemia persisting for at least 3 days (e.g., for at least 7 days) despite maximal replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily;

(c) upon the patient having Grade 3 or 4 hypokalemia despite maximal replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily;

(d) upon the patient having an alanine transaminase (ALT) or aspartate aminotransferase (AST) of 3 to 5 times upper limit of normal (ULN) (Grade 2), withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily; and (e) upon the patient having an ALT or AST of greater than 5 times ULN (Grade 3 or 4), permanently discontinuing treatment with the nirogacestat or pharmaceutically acceptable salt thereof.

In one embodiment, the method further comprises:

(f) for another severe adverse reaction (that is, a severe adverse reaction other than those specified in steps (a)

through (c)), life-threatening adverse reaction, or persistent intolerable Grade 2 adverse event, withholding the nirogacestat or pharmaceutically acceptable salt thereof until the adverse reaction is resolved to no higher than a Grade 1 adverse reaction or baseline and then, after considering the potential benefit and likelihood of recurrence of the adverse reaction, (A) restarting oral administration of the nirogacestat or pharmaceutically acceptable salt thereof at a dose of 100 mg (free base equivalent dose) twice daily and (B) upon recurrence of the severe or life-threatening adverse reaction at the 100 mg (free base equivalent dose) twice daily dose, permanently discontinuing treatment with the nirogacestat or pharmaceutically acceptable salt thereof.

In another embodiment, the method comprises (a) upon the patient having Grade 3 or 4 diarrhea persisting for at least 3 days despite maximal medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily.

In yet another embodiment, the method comprises (b) upon the patient having a Grade 3 or 4 hypophosphatemia persisting for at least 3 days (e.g., for at least 7 days) despite maximal replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily.

In yet another embodiment, the method comprises (c) upon the patient having a Grade 3 or 4 hypokalemia despite maximal replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily.

In yet another embodiment, the method comprises (d) upon the patient having an ALT or AST of 3 to 5 times ULN, withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily.

In yet another embodiment, the method comprises (e) upon the patient having an ALT or AST of greater than 5 times ULN, permanently discontinuing treatment with the nirogacestat or pharmaceutically acceptable salt thereof.

In yet another embodiment, the method comprises:

(a) upon the patient having Grade 3 or 4 diarrhea persisting for at least 3 days despite maximal medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily;

(b) upon the patient having Grade 3 or 4 hypophosphatemia persisting for at least 3 days (e.g., for at least 7 days) despite maximal replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily;

(c) upon the patient having Grade 3 or 4 hypokalemia despite maximal replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily;

(d) upon the patient having an ALT or AST of 3 to 5 times ULN, withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily; and (e) upon the patient having an ALT or AST of greater than 5 times ULN, permanently discontinuing treatment with the nirogacestat or pharmaceutically acceptable salt thereof.

In yet another embodiment, the method comprises:

(a) upon the patient having Grade 3 or 4 diarrhea persisting for at least 3 days despite maximal medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily;

(b) upon the patient having Grade 3 or 4 hypophosphatemia persisting for at least 3 days (e.g., for at least 7 days) despite maximal replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily;

(c) upon the patient having Grade 3 or 4 hypokalemia despite maximal replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily;

(d) upon the patient having an ALT or AST of 3 to 5 times ULN, withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily;

(e) upon the patient having an ALT or AST of greater than 5 times ULN, permanently discontinuing treatment with the nirogacestat or pharmaceutically acceptable salt thereof; and (f) for another severe adverse reaction, life-threatening adverse reaction, or persistent intolerable Grade 2 adverse event, withholding the nirogacestat or pharmaceutically acceptable salt thereof until the adverse reaction is resolved to no higher than a Grade 1 adverse reaction or baseline and then, after considering the potential benefit and likelihood of recurrence of the adverse reaction, (A) restarting oral administration of the nirogacestat or pharmaceutically acceptable salt thereof at a dose of 100 mg (free base equivalent dose) twice daily and (B) upon recurrence of the severe or life-threatening adverse reaction at the 100 mg (free base equivalent dose) twice daily dose, permanently discontinuing treatment with the nirogacestat or pharmaceutically acceptable salt thereof.

In yet another embodiment, upon the patient having a Grade 3 dermatologic reaction, withholding the nirogacestat or pharmaceutically acceptable salt thereof until the dermatologic reaction is resolved to no higher than a Grade 1 dermatologic reaction and then restarting oral administration of the nirogacestat or pharmaceutically acceptable salt thereof at a dose of 100 mg (free base equivalent dose) twice daily.

In yet another embodiment of any of the methods described herein, in the event the patient vomits or misses a dose, the patient is administered the next dose at its scheduled time.

In yet another embodiment of any of the methods described herein, the methods comprise avoiding concomitant use of nirogacestat (or a pharmaceutically acceptable salt thereof) with strong or moderate CYP3A inhibitors including grapefruit products, Seville oranges, and starfruit.

In yet another embodiment of any of the methods described herein, the methods comprise avoiding concomitant use of nirogacestat (or a pharmaceutically acceptable salt thereof) with strong or moderate CYP3A inducers.

In yet another embodiment of any of the methods described herein, the methods comprise avoiding concomitant use of nirogacestat (or a pharmaceutically acceptable salt thereof) with proton pump inhibitors and H2 blockers. If concomitant use cannot be avoided, nirogacestat (or a pharmaceutically acceptable salt thereof) can be staggered with antacids (e.g., administer OGSIVEO 2 hours before or 2 hours after antacid use).

In yet another embodiment of any of the methods described herein, the patient (e.g., an adult patient) has progressing ovarian cancer. In one embodiment, the patient (e.g., an adult patient) has progressing ovarian cancer that is deemed not amenable to surgery (e.g., without the risk of significant morbidity).

In yet another embodiment of any of the methods described herein, the patient (e.g., an adult patient) has progressing ovarian granulosa cell tumors. In one embodiment, the patient (e.g., an adult patient) has progressing ovarian granulosa cell tumors that is deemed not amenable to surgery (e.g., without the risk of significant morbidity).

In yet another embodiment of any of the methods described herein, the patient has a mutation in the adenomatous polyposis coli (APC) tumor suppressor gene.

In yet another embodiment of any of the methods described herein, the patient has a mutation in the CTNNB1 (β-catenin) gene.

In yet another embodiment of any of the methods described herein, the patient was previously treated with one or more tyrosine kinase inhibitors (such as sorafenib, pazopanib, sunitinib, imatinib, dasatinib, nilotinib, bosutinib, asciminib, and ponatinib).

In yet another embodiment of any of the methods described herein, the patient is an adult.

In yet another embodiment of any of the methods described herein, the patient has progressing ovarian cancer, such as an adult patient having progressing ovarian cancer.

In yet another embodiment of any of the methods described herein, the patient has refractory or recurrent disease after previous treatment.

In yet another embodiment of any of the methods described herein, the patient is a treatment naïve patient.

In yet another embodiment of any of the methods described herein, the patient is a post-menopausal woman.

In yet another embodiment of any of the methods described herein, the patient is a woman, such as a woman who is 15 to 60 years old.

In yet another embodiment of any of the methods described herein, the patient uses contraception during treatment with nirogacestat or a pharmaceutically acceptable salt thereof.

In yet another embodiment of any of the methods described herein, the patient is a female who is not of childbearing potential.

In yet another embodiment of any of the methods described herein, the patient is a female who is of childbearing potential and, during treatment with nirogacestat or a pharmaceutically acceptable salt thereof, is abstinent from sexual intercourse or uses contraception. In one embodiment, the female patient who is of childbearing potential remains abstinent or continues use of contraception until 1 week, 1 month, or 6 months after the last dose of nirogacestat or a pharmaceutically acceptable salt thereof.

In yet another embodiment of any of the methods described herein, gastric acid reducing agents are avoided or administered 4 hours after administration of the nirogacestat or pharmaceutically acceptable salt thereof.

Yet another embodiment is a method for treating ovarian cancer (e.g., ovarian granulosa cell tumors) in a treatment naïve patient comprising orally administering to the patient 150 mg (free base equivalent dose) of nirogacestat or a pharmaceutically acceptable salt thereof twice daily.

In yet another embodiment of any of the methods described herein, the nirogacestat or pharmaceutically acceptable salt thereof is nirogacestat dihydrobromide.

In yet another embodiment of any of the methods described herein, the patient, after initial administration of 150 mg (free base equivalent dose) of nirogacestat or a pharmaceutically acceptable salt thereof, exhibits a $C_{max}$ of nirogacestat of from about 480 to about 950 ng/mL.

In yet another embodiment of any of the methods described herein, the patient, after initial administration of 150 mg (free base equivalent dose) of nirogacestat or a pharmaceutically acceptable salt thereof, exhibits a $C_{max}$ of nirogacestat of from about 550 to about 1100 ng/mL.

In yet another embodiment of any of the methods described herein, the patient, after initial administration of 150 mg (free base equivalent dose) of nirogacestat or a pharmaceutically acceptable salt thereof, exhibits a $C_{max}$ of nirogacestat of from about 600 to about 800 ng/ml.

In yet another embodiment of any of the methods described herein, the patient exhibits, after initial administration of 150 mg (free base equivalent dose) of nirogacestat or a pharmaceutically acceptable salt thereof, an $AUC_{last}$ of nirogacestat of less than 4000 ng·h/mL. In one embodiment, the patient exhibits, after initial administration of 150 mg (free base equivalent dose) of nirogacestat or a pharmaceutically acceptable salt thereof, an $AUC_{last}$ of nirogacestat of less than 4000 ng·h/mL and a $C_{max}$ of nirogacestat of from about 480 to about 950 ng/mL.

In yet another embodiment of any of the methods described herein, the patient exhibits, after initial administration of 150 mg (free base equivalent dose) of nirogacestat or a pharmaceutically acceptable salt thereof, an $AUC_{last}$ of nirogacestat of from about 2000 to about 4000 ng·h/mL. In one embodiment, the patient exhibits, after initial administration of 150 mg (free base equivalent dose) of nirogacestat or a pharmaceutically acceptable salt thereof, an $AUC_{last}$ of nirogacestat of from about 2000 to about 4000 ng·h/mL and a $C_{max}$ of nirogacestat of from about 480 to about 950 ng/mL.

In yet another embodiment of any of the methods described herein, the patient exhibits, after initial administration of 150 mg (free base equivalent dose) of nirogacestat or a pharmaceutically acceptable salt thereof, an $AUC_{inf}$ of nirogacestat of less than 4000 ng·h/mL. In one embodiment, the patient exhibits, after initial administration of 150 mg (free base equivalent dose) of nirogacestat or a pharmaceutically acceptable salt thereof, an $AUC_{inf}$ of nirogacestat of less than 4000 ng·h/mL and a $C_{max}$ of nirogacestat of from about 480 to about 950 ng/ml.

In yet another embodiment of any of the methods described herein, the patient exhibits, after initial administration of 150 mg (free base equivalent dose) of nirogacestat or a pharmaceutically acceptable salt thereof, an $AUC_{inf}$ of nirogacestat of from about 2000 to about 4000 ng·h/mL. In one embodiment, the patient exhibits, after initial administration of 150 mg (free base equivalent dose) of nirogacestat or a pharmaceutically acceptable salt thereof, an $AUC_{inf}$ of nirogacestat of from about 2000 to about 4000 ng·h/mL and a $C_{max}$ of nirogacestat of from about 480 to about 950 ng/mL.

In yet another embodiment of any of the methods described herein, the patient exhibits, after initial administration of 150 mg (free base equivalent dose) of nirogacestat or a pharmaceutically acceptable salt thereof, an $AUC_{inf}$ of nirogacestat of from about 2200 to about 4800 ng·h/mL.

In yet another embodiment of any of the methods described herein, the patient exhibits, after initial administration of 150 mg (free base equivalent dose) of nirogacestat or a pharmaceutically acceptable salt thereof, an $AUC_{inf}$ of nirogacestat of from about 2200 to about 3300 ng·h/mL.

In yet another embodiment of any of the methods described herein, the patient exhibits, at steady state exposure from administration of 150 mg (free base equivalent dose) of nirogacestat or a pharmaceutically acceptable salt thereof twice daily, a $C_{max}$ of nirogacestat of from about 300 to about 700 ng/mL, such as from about 350 to about 650 ng/mL.

In yet another embodiment of any of the methods described herein, the patient exhibits, at steady state exposure from administration of 150 mg (free base equivalent dose) of nirogacestat or a pharmaceutically acceptable salt thereof twice daily, a $C_{max}$ of nirogacestat of from about 400 to about 600 ng/mL.

In yet another embodiment of any of the methods described herein, the patient exhibits, at steady state exposure from administration of 150 mg (free base equivalent dose) of nirogacestat or a pharmaceutically acceptable salt thereof twice daily, an $AUC_{tau}$ of nirogacestat of from about 2200 to about 4800 ng·h/mL, such as from about 2500 to 4000 ng·h/mL.

In yet another embodiment of any of the methods described herein, the patient exhibits, at steady state exposure from administration of 150 mg (free base equivalent dose) of nirogacestat or a pharmaceutically acceptable salt thereof twice daily, an $AUC_{tau}$ of nirogacestat of from about 3000 to about 3700 ng·h/mL.

In one embodiment of any of the methods described herein, the patient is treated with 100 mg (free base equivalent dose) of nirogacestat or a pharmaceutically acceptable salt thereof twice daily, which is reduced to 50 mg (free base equivalent dose) of nirogacestat or a pharmaceutically acceptable salt thereof twice daily instead of 100 mg twice daily in the event of the specified adverse reactions.

One embodiment is a method for treating a condition responsive to inhibition of gamma secretase, such as ovarian cancer (e.g., ovarian granulosa cell tumors), in a patient in need thereof comprising orally administering to the patient 150 mg (free base equivalent dose) of nirogacestat or a pharmaceutically acceptable salt thereof twice daily, where the method comprises one or more of:

(a) upon the patient having a Grade 3 diarrhea persisting for at least 3 days despite maximal medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily;

(b) upon the patient having a Grade 3 folliculitis, withholding the nirogacestat or pharmaceutically acceptable salt thereof until the folliculitis is resolved to no higher than a Grade 1 folliculitis or baseline and then restarting oral administration of the nirogacestat or pharmaceutically acceptable salt thereof at a dose of 100 mg (free base equivalent dose) twice daily;

(c) upon the patient having a Grade 3 maculopapular rash, withholding the nirogacestat or pharmaceutically acceptable salt thereof until the maculopapular rash is resolved to no higher than a Grade 1 maculopapular rash or baseline and then restarting oral administration of the nirogacestat or pharmaceutically acceptable salt thereof at a dose of 100 mg (free base equivalent dose) twice daily;

(d) upon the patient having a Grade 3 hidradenitis, withholding the nirogacestat or pharmaceutically acceptable salt thereof until the hidradenitis is resolved to no higher than a Grade 1 hidradenitis or baseline and then restarting oral administration of the nirogacestat or pharmaceutically acceptable salt thereof at a dose of 100 mg (free base equivalent dose) twice daily;

(e) upon the patient having Grade 3 hypophosphatemia persisting for at least 7 days despite maximal replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily;

(f) upon the patient having Grade 3 hypokalemia despite maximal replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily; and (g) upon the patient having an alanine transaminase (ALT) or aspartate aminotransferase (AST) of 3 to 5 times upper limit of normal (ULN), withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily.

In one embodiment, the method further comprises one or more of:

(h) upon the patient having an ALT or AST of greater than 5 times ULN, permanently discontinuing treatment with the nirogacestat or pharmaceutically acceptable salt thereof;

(i) upon the patient having anaphylaxis or other severe hypersensitivity reaction, permanently discontinuing treatment with the nirogacestat or pharmaceutically acceptable salt thereof; and (j) for another severe adverse reaction, life-threatening adverse reaction, or persistent intolerable Grade 2 adverse event, withholding the nirogacestat or pharmaceutically acceptable salt thereof until the adverse reaction is resolved to no higher than a Grade 1 adverse reaction or baseline and then, after considering the potential benefit and likelihood of recurrence of the adverse reaction, (A) restarting oral administration of the nirogacestat or pharmaceutically acceptable salt thereof at a dose of 100 mg (free base equivalent dose) twice daily and (B) upon recurrence of the severe or life-threatening adverse reaction at the 100 mg (free base equivalent dose) twice daily dose, permanently discontinuing treatment with the nirogacestat or pharmaceutically acceptable salt thereof.

Compositions comprising a compound of Formula (I)

(I)

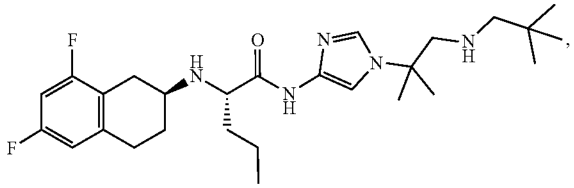

or a pharmaceutically acceptable salt thereof wherein the composition provides a mean maximum drug plasma concentration ($C_{rax}$) of more than 100 ng/ml are described herein.

Additionally, methods for treating ovarian cancer (e.g., ovarian granulosa cell tumors) comprising administration to a patient in need thereof an oral dosage form comprising 50 mg of nirogacestat or a pharmaceutically acceptable salt thereof to a patient in need thereof are described herein.

Also, methods for treating ovarian cancer (e.g., ovarian granulosa cell tumors) in a patient in need thereof comprising administering to the patient a 50 mg oral dosage of nirogacestat or a pharmaceutically acceptable salt thereof wherein the oral dosage provides a mean maximum drug plasma concentration ($C_{max}$) of more than 100 ng/ml are described herein.

Furthermore, methods for treating ovarian cancer (e.g., ovarian granulosa cell tumors) in a patient in need thereof comprising administering to the patient a 50 mg oral dosage of nirogacestat or a pharmaceutically acceptable salt thereof wherein the oral dosage provides an in vivo area under the plasma curve ($AUC_{inf}$) of less than 700 ng·h/ml.

Methods for treating ovarian cancer (e.g., ovarian granulosa cell tumors) comprising administration to a patient in need thereof 300 mg per day of nirogacestat or a pharmaceutically acceptable salt thereof to a patient in need thereof are also disclosed herein.

Moreover, methods for treating ovarian cancer (e.g., ovarian granulosa cell tumors) in a patient in need thereof comprising administering to the patient an oral dosage of nirogacestat or a pharmaceutically acceptable salt thereof wherein the oral dosage provides a mean maximum drug plasma concentration ($C_{max}$) of more than 100 ng/ml are disclosed herein.

Methods for treating ovarian cancer (e.g., ovarian granulosa cell tumors) in a patient in need thereof comprising administering to the patient an oral dosage of nirogacestat or a pharmaceutically acceptable salt thereof wherein the oral dosage provides an in vivo area under the plasma curve ($AUC_{inf}$) of less than 700 ng·h/ml are also disclosed herein.

Additionally, methods for treating ovarian cancer (e.g., ovarian granulosa cell tumors) comprising administration to a patient in need thereof 200 mg per day of nirogacestat or a pharmaceutically acceptable salt thereof to a patient in need thereof are disclosed herein.

Also, methods for treating ovarian cancer (e.g., ovarian granulosa cell tumors) comprising administration to a patient in need thereof 100 mg per day of nirogacestat or a pharmaceutically acceptable salt thereof to a patient in need thereof are disclosed herein.

Methods for treating ovarian cancer (e.g., ovarian granulosa cell tumors) comprising once daily administration of 200 mg nirogacestat or a pharmaceutically acceptable salt thereof to a patient in need thereof are also disclosed herein.

Furthermore, methods for treating ovarian cancer (e.g., ovarian granulosa cell tumors) comprising once daily administration of 150 mg (free base equivalent dose) nirogacestat or a pharmaceutically acceptable salt thereof to a patient in need thereof.

Methods for treating ovarian cancer (e.g., ovarian granulosa cell tumors) comprising once daily administration of 100 mg nirogacestat or a pharmaceutically acceptable salt thereof to a patient in need thereof are also disclosed herein.

Additionally, methods for treating ovarian cancer (e.g., ovarian granulosa cell tumors) comprising once daily administration of 50 mg nirogacestat or a pharmaceutically acceptable salt thereof to a patient in need thereof are disclosed herein.

Also, methods for treating ovarian cancer (e.g., ovarian granulosa cell tumors) in a patient in need thereof comprising administering to the patient a 50 mg oral dosage of nirogacestat or a pharmaceutically acceptable salt thereof wherein the oral dosage provides a mean maximum drug plasma concentration ($C_{max}$) of more than 100 ng/ml.

Further, methods for treating ovarian cancer (e.g., ovarian granulosa cell tumors) in a patient in need thereof comprising administering to the patient a 100 mg oral dosage of nirogacestat or a pharmaceutically acceptable salt thereof wherein the oral dosage provides a mean maximum drug plasma concentration ($C_{max}$) of more than 225 ng/ml.

Methods for treating ovarian cancer (e.g., ovarian granulosa cell tumors) in a patient in need thereof comprising administering to the patient a 50 mg oral dosage of nirogacestat or a pharmaceutically acceptable salt thereof wherein the oral dosage provides an in vivo area under the plasma curve ($AUC_{inf}$) of less than 700 ng·h/ml are also disclosed herein.

Additionally, methods for treating ovarian cancer (e.g., ovarian granulosa cell tumors) in a patient in need thereof comprising administering to the patient a 100 mg oral dosage of nirogacestat or a pharmaceutically acceptable salt thereof wherein the oral dosage provides an in vivo area under the plasma curve ($AUC_{inf}$) of less than 3000 ng·h/ml are disclosed herein.

Methods for treating ovarian cancer (e.g., ovarian granulosa cell tumors) in a patient in need thereof comprising administering to the patient an oral dosage of nirogacestat or a pharmaceutically acceptable salt thereof wherein the oral dosage provides a mean maximum drug plasma concentration ($C_{max}$) of more than 100 ng/ml are also disclosed herein.

Additionally, methods for treating ovarian cancer (e.g., ovarian granulosa cell tumors) in a patient in need thereof comprising administering to the patient an oral dosage of nirogacestat or a pharmaceutically acceptable salt thereof wherein the oral dosage provides a mean maximum drug plasma concentration ($C_{max}$) of more than 225 ng/ml are disclosed herein.

Further, methods for treating ovarian cancer (e.g., ovarian granulosa cell tumors) in a patient in need thereof comprising administering to the patient an oral dosage of nirogacestat or a pharmaceutically acceptable salt thereof wherein the oral dosage provides an in vivo area under the plasma curve ($AUC_{inf}$) of less than 700 ng·h/ml are disclosed herein.

Methods for treating ovarian cancer (e.g., ovarian granulosa cell tumors) in a patient in need thereof comprising administering to the patient an oral dosage of nirogacestat or a pharmaceutically acceptable salt thereof wherein the oral dosage provides an in vivo area under the plasma curve ($AUC_{inf}$) of less than 3000 ng·h/ml are also disclosed herein.

Also, methods for treating ovarian cancer (e.g., ovarian granulosa cell tumors) in a patient in need thereof comprising administering to the patient a single oral dosage of nirogacestat or a pharmaceutically acceptable salt thereof for the concomitant treatment of ovarian cancer (e.g., ovarian granulosa cell tumors) are disclosed herein.

Methods for treating ovarian cancer (e.g., ovarian granulosa cell tumors) in a patient in need thereof comprising administering to the patient an oral dosage of nirogacestat or a pharmaceutically acceptable salt thereof in combination with belantamab mafodotin are also disclosed herein.

Yet another embodiment is a method for treating ovarian cancer (e.g., ovarian granulosa cell tumors) in a patient in need thereof comprising concomitantly administering to the patient (i) nirogacestat or a pharmaceutically acceptable salt thereof and (ii) one or more additional active ingredients for treating ovarian cancer (e.g., ovarian granulosa cell tumors) (e.g., a BCMA therapy (for instance, administered intravenously)), where the method comprises (A) orally administering to the patient 150 mg (free base equivalent dose) of nirogacestat or a pharmaceutically acceptable salt thereof twice daily and (B) one or more of:

(a) upon the patient having Grade 3 or 4 diarrhea persisting for at least 3 days despite maximal medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily;

(b) upon the patient having Grade 3 or 4 hypophosphatemia persisting for at least 3 days (e.g., for at least 7 days) despite maximal replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily;

(f) upon the patient having Grade 3 or 4 hypokalemia despite maximal replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily;

(d) upon the patient having an alanine transaminase (ALT) or aspartate aminotransferase (AST) of 3 to 5 times upper limit of normal (ULN), withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily; and (e) upon the patient having an ALT or AST of greater than 5 times ULN, permanently discontinuing treatment with the nirogacestat or pharmaceutically acceptable salt thereof. In one preferred embodiment, the patient is concomitantly administered a BCMA therapy. In another embodiment, the method further comprises (h) for another severe adverse reaction, life-threatening adverse reaction, or persistent intolerable Grade 2 adverse event, withholding the nirogacestat or pharmaceutically acceptable salt thereof until the adverse reaction is resolved to no higher than a Grade 1 adverse reaction or baseline and then, after considering the potential benefit and likelihood of recurrence of the adverse reaction, (A) restarting oral administration of the nirogacestat or pharmaceutically acceptable salt thereof at a dose of 100 mg (free base equivalent dose) twice daily and (B) upon recurrence of the severe or life-threatening adverse reaction at the 100 mg (free base equivalent dose) twice daily dose, permanently discontinuing treatment with the nirogacestat or pharmaceutically acceptable salt thereof.

Yet another embodiment is a method for treating ovarian cancer (e.g., ovarian granulosa cell tumors) in a patient in need thereof comprising concomitantly administering to the patient (i) nirogacestat or a pharmaceutically acceptable salt thereof and (ii) one or more additional active ingredients for treating ovarian cancer (e.g., ovarian granulosa cell tumors) (e.g., a BCMA therapy), where the method comprises (A) orally administering to the patient 100 mg (free base equivalent dose) of nirogacestat or a pharmaceutically acceptable salt thereof twice daily and (B) one or more of:

(a) upon the patient having Grade 3 or 4 diarrhea persisting for at least 3 days despite maximal medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 50 mg (free base equivalent dose) twice daily;

(b) upon the patient having Grade 3 or 4 hypophosphatemia persisting for at least 3 days (e.g., for at least 7 days) despite maximal replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 50 mg (free base equivalent dose) twice daily;

(c) upon the patient having Grade 3 or 4 hypokalemia despite maximal replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 50 mg (free base equivalent dose) twice daily;

(d) upon the patient having an alanine transaminase (ALT) or aspartate aminotransferase (AST) of 3 to 5 times upper limit of normal (ULN), withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 50 mg (free base equivalent dose) twice daily; and (e) upon the patient having an ALT or AST of greater than 5 times ULN, permanently discontinuing treatment with the nirogacestat or pharmaceutically acceptable salt thereof. In one preferred embodiment, the patient is concomitantly administered a BCMA therapy. In another embodiment, the method further comprises (h) for another severe adverse reaction, life-threatening adverse reaction, or persistent intolerable Grade 2 adverse event, withholding the nirogacestat or pharmaceutically acceptable salt thereof until the adverse reaction is resolved to no higher than a Grade 1 adverse reaction or baseline and then, after considering the potential benefit and likelihood of recurrence of the adverse reaction, (A) restarting oral administration of the nirogacestat or pharmaceutically acceptable salt thereof at a dose of 50 mg (free base equivalent dose) twice daily and (B) upon recurrence of the severe or life-threatening adverse reaction at the 50 mg (free base equivalent dose) twice daily dose, permanently discontinuing treatment with the nirogacestat or pharmaceutically acceptable salt thereof.

In one embodiment of any of the methods described herein, the ovarian cancer is epithelial ovarian cancer. In some instances, the epithelial ovarian cancer is a serous carcinoma. In some instances, the epithelial ovarian cancer is a endometrioid carcinoma. In some instances, the epithelial ovarian cancer is a mucinous carcinoma. In some instances, the epithelial ovarian cancer is a clear cell carcinoma.

In another embodiment of any of the methods described herein, the ovarian cancer is germ cell ovarian tumor. In some instances, the germ cell ovarian tumor is a teratoma. In some instances, the germ cell ovarian tumor is a dysgerminoma. In some instances, the germ cell ovarian tumor is a endodermal sinus tumor. In some instances, the germ cell ovarian tumor is a choriocarcinoma tumor.

In yet another embodiment of any of the methods described herein, the ovarian cancer is ovarian sarcoma. In yet another embodiment of any of the methods described herein, the ovarian cancer is a krukenberg tumor. In yet another embodiment of any of the methods described herein, the ovarian cancer is a small cell carcinoma (SCCO). In yet another embodiment of any of the methods described herein, the ovarian cancer is a stromal cell ovarian cancer. In yet another embodiment of any of the methods described herein, the ovarian cancer is a Sertoli-Leydig Cell tumor. In some instances, the ovarian cancer is ovarian carcinosarcoma. In yet another embodiment of any of the methods described herein, the ovarian cancer is ovarian sex cord stromal tumors (SCSTs). In yet another embodiment of any of the methods described herein, the ovarian cancer is ovarian granulosa cell tumors (OvGCT). In yet another embodiment of any of the methods described herein, the ovarian cancer is borderline ovarian tumors. In yet another embodiment of any of the methods described herein, the ovarian cancer is stromal cell tumors.

In some aspects, the pharmaceutically acceptable salt form of nirogacestat in the composition, dosage forms, or methods of treatments described herein is a hydrobromide salt form. In some aspects, the hydrobromide salt form is a dihydrobromide salt form.

In some aspects, the compositions or dosages are orally administered to a human. In some aspects, the compositions or dosages are in the form of a solid. In some aspects, the compositions or dosages are in the form of tablets or capsules.

In yet another embodiment of any of the methods described herein, one or more anti-emetic drugs and/or one or more anti-diarrheal drugs may be administered to the patient while being treated with nirogacestat.

In some aspects, the ovarian cancer is an ovarian granulosa cell tumor. In some aspects, the patient exhibits hyperestrogenism.

DETAILED DESCRIPTION OF THE INVENTION

I. Definitions

To facilitate understanding of the disclosure set forth herein, a number of terms are defined below.

Generally, the nomenclature used herein and the laboratory procedures in organic chemistry, medicinal chemistry, and pharmacology described herein are those well-known and commonly employed in the art. Unless defined otherwise, all technical and scientific terms used herein generally have the same meaning as commonly understood by one of ordinary skill in the art to which this disclosure belongs.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

The term "nirogacestat" refers to the single enantiomer (S)-2-(((S)-6,8-difluoro-1,2,3,4-tetrahydronaphthalen-2-yl)amino)-N-(1-(2-methyl-1-(neopentylamino) propan-2-yl)-1H-imidazol-4-yl)pentanamide. A preferred pharmaceutically acceptable salt of nirogacestat is nirogacestat dihydrobromide (which is also referred to as nirogacestat hydrobromide). All amounts of nirogacestat or its salt for administration are in terms of its free base. For instance, 150 mg nirogacestat dihydrobromide refers to an amount of nirogacestat dihydrobromide which is equivalent to 150 mg nirogacestat free base (that is, approximately, 199.6 mg nirogacestat dihydrobromide).

The term "subject" refers to an animal, including, but not limited to, a primate (e.g., human), cow, sheep, goat, horse, dog, cat, rabbit, rat, or mouse. The terms "subject" and "patient" are used interchangeably herein in reference, for example, to a mammalian subject, such as a human subject.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Thus, those in need of treatment include those already diagnosed with or suspected of having the disorder. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. The term "therapeutically effective amount" is meant to include the amount of a compound that, when administered, is sufficient to prevent development of, or alleviate to some extent, one or more of the symptoms of a disorder, disease, or condition being treated. The term "therapeutically effective amount" also refers to the amount of a compound that is sufficient to elicit the biological or medical response of a cell, tissue, system, animal, or human, which is being sought by a researcher, veterinarian, medical doctor, or clinician.

In certain aspects, a subject is successfully "treated" for cancer, e.g., ovarian cancer, according to the methods of the present invention if the patient shows one or more of the following: a reduction in the number of or complete absence of cancer cells; relief of one or more symptoms associated with the specific cancer; reduced morbidity and mortality; improvement in quality of life; increased progression-free survival ("PFS"), disease-free survival ("DFS"), overall survival ("OS"), metastasis-free survival ("MFS"), complete response ("CR"), minimal residual disease ("MRD"), partial response ("PR"), stable disease ("SD"), a decrease in progressive disease ("PD"), an increased time to progression ("TTP"), or any combination thereof. In some aspects, nationally or internationally accepted standards of treatment outcomes in a given cancer can be used to determine whether the therapeutically effective amount nirogacestat or a pharmaceutically acceptable salt thereof meets any of these particular endpoints (e.g., CR, PFS, PR)

The terms "pharmaceutically acceptable carrier," "pharmaceutically acceptable excipient," "physiologically acceptable carrier," or "physiologically acceptable excipient" refer to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See *Remington: The Science and Practice of Pharmacy,* 21st Edition, Lippincott Williams & Wilkins: Philadelphia, PA, 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; Pharmaceutical Preformulation and Formulation, Gibson Ed., CRC Press LLC: Boca Raton, FL, 2004 (incorporated herein by reference).

The term "pharmaceutically-acceptable salts" refers to the relatively non-toxic, inorganic and organic acid addition salts of Compound A or Compound B. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In certain aspects, the compounds of the present invention may contain one or more acidic functional groups and, thus, are capable of forming pharmaceutically acceptable salts with pharmaceutically acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra).

The term "baseline" refers to an initial measurement of a condition that is taken at an early time point and used for comparison over time to look for changes. Baseline may be a measurement just before treatment and used afterwards to see if the treatment had an effect. For example, the size of a tumor can be measured before treatment (baseline) and then afterwards to see if the treatment had an effect.

The terms "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The term "treatment naïve patient" refers to a patient suffering from a particular disorder or disease (such as ovarian cancer) that has not previously undergone treatment for that disorder or disease. In one embodiment, the treatment naïve patient has not previously undergone surgery. In another embodiment, the treatment naïve patient has not been treated with a pharmaceutical agent. In an exemplary embodiment, the treatment naïve patient has not been treated with a tyrosine kinase inhibitor.

Unless the context requires otherwise, the terms "comprise," "comprises," and "comprising" are used on the basis and clear understanding that they are to be interpreted inclusively, rather than exclusively, and that Applicant intends each of those words to be so interpreted in construing this patent, including the claims below.

II. Compositions

The present disclosure relates to compositions comprising a compound of Formula (I)

(I)

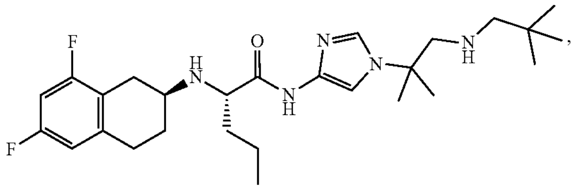

or a pharmaceutically acceptable salt thereof wherein the composition provides a mean maximum drug plasma concentration ($C_{max}$) of more than 100 ng/ml. In some aspects, the compositions comprising a compound of Formula (I) or a pharmaceutically acceptable salt thereof provide a mean maximum drug plasma concentration ($C_{max}$) of about 150 ng/ml to about 500 ng/ml. In some aspects, the compositions comprising a compound of Formula (I) or a pharmaceutically acceptable salt thereof provide a mean maximum drug plasma concentration ($C_{max}$) of about 200 ng/ml to about 450 ng/ml. In some aspects, the compositions comprising a compound of Formula (I) or a pharmaceutically acceptable salt thereof provide a mean maximum drug plasma concentration ($C_{max}$) of about 250 ng/ml to about 400 ng/ml. In some aspects, the compositions comprising a compound of Formula (I) or a pharmaceutically acceptable salt thereof provide a mean maximum drug plasma concentration ($C_{max}$) of about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/l, about 425 ng/ml, about 450 ng/ml, about 475 ng/ml, or about 500 ng/ml.

In some aspects, the pharmaceutically acceptable salt of the compound of Formula (I) is the hydrobromide salt. In some aspects, the pharmaceutically acceptable salt of the compound of Formula (I) is the dihydrobromide salt.

In some aspects, the compositions comprise a compound of Formula (I) as a dihydrobromide salt form and provide a mean maximum drug plasma concentration ($C_{max}$) of more than 100 ng/ml. In some aspects, the compositions comprise a compound of Formula (I) as a dihydrobromide salt form and provide a mean maximum drug plasma concentration ($C_{max}$) of about 150 ng/ml to about 500 ng/ml. In some aspects, the compositions comprise a compound of Formula (I) as a dihydrobromide salt form and provide a mean maximum drug plasma concentration ($C_{max}$) of about 200 ng/ml to about 450 ng/ml. In some aspects, the compositions comprise a compound of Formula (I) as a dihydrobromide salt form and provide a mean maximum drug plasma concentration ($C_{max}$) of about 250 ng/ml to about 400 ng/ml. In some aspects, the compositions comprise a compound of Formula (I) as a dihydrobromide salt form and provide a mean maximum drug plasma concentration ($C_{max}$) of about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/1, about 425 ng/ml, about 450 ng/ml, about 475 ng/ml, or about 500 ng/ml.

The compositions comprising the compound of Formula (I) or pharmaceutically acceptable salt thereof (e.g., dihydrobromide salt form) can be administered to subjects via the oral, parenteral (such as subcutaneous, intravenous, intramuscular, intrasternal and infusion techniques), rectal, intranasal, topical or transdermal (e.g., through the use of a patch) routes. In some aspects, the compositions comprising the compound of Formula (I) or pharmaceutically acceptable salt thereof (e.g., dihydrobromide salt form) can be administered to subjects orally.

In some aspects, the compositions comprising the compound of Formula (I) or pharmaceutically acceptable salt thereof (e.g., dihydrobromide salt form) are in the form of a solid. In one aspect, the compositions comprising the compound of Formula (I) or pharmaceutically acceptable salt thereof (e.g., dihydrobromide salt form) are a tablet or capsule.

In some aspects, the compositions comprising the compound of Formula (I) or pharmaceutically acceptable salt thereof (e.g., dihydrobromide salt form) can additionally comprise one or more pharmaceutically acceptable excipients. For example, for oral administration, microcrystalline cellulose, sodium citrate, calcium carbonate, dicalcium phosphate and glycine may be employed along with various disintegrants such as starch (preferably corn, potato or tapioca starch), methylcellulose, alginic acid and certain complex silicates, together with granulation binders such as polyvinylpyrrolidone, sucrose, gelatin and acacia, can be included in a tablet. Additionally, lubricating agents such as magnesium stearate, sodium lauryl sulfate and talc are often useful for tableting purposes. Solid compositions of a similar type may also be employed as fillers in gelatin capsules. Preferred materials in this connection include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

In some aspects, the compositions comprising the compound of Formula (I) or pharmaceutically acceptable salt thereof (e.g., dihydrobromide salt form) may be administered to a patient in need thereof for the treatment of ovarian cancer. The compositions may include amounts of the compound of Formula (I) or pharmaceutically acceptable salt thereof (e.g., dihydrobromide salt form) in the range of about, e.g., 25 mg to 350 mg, 50 mg to 325 mg, 75 mg to 300 mg, 100 mg to 275 mg, 125 mg to 250 mg, 150 mg to 225 mg, 175 mg to 200 mg. In some aspects, the compositions comprising the compound of Formula (I) or pharmaceutically acceptable salt thereof (e.g., dihydrobromide salt form) may be administered in the range of about, e.g., 50 mg to 300 mg, 100 mg to 250 mg, and 150 mg to 200 mg. The compositions may include amounts of the compound of Formula (I) or pharmaceutically acceptable salt thereof (e.g., dihydrobromide salt form) of about, e.g., 25 mg, 50 mg, 75 mg, 100 mg, 125 mg, 150 mg, 175 mg, 200 mg, 225 mg, 250 mg, 275 mg, 300 mg, 325 mg and 350 mg. In some aspects, the compositions may include amounts of the compound of Formula (I) or pharmaceutically acceptable salt thereof (e.g., dihydrobromide salt form) of about, e.g., 50 mg, 100 mg, 150 mg, 200 mg, 250 mg, 300 mg, and 350 mg. In some aspects, the compositions may be administered once daily. In other aspects, the compositions may be administered twice daily. For example, the compositions may include 50 mg nirogacestat or a pharmaceutically acceptable salt thereof and be administered once daily. In other examples, the compositions may include 50 mg nirogacestat or a pharmaceutically acceptable salt thereof and be administered twice daily. The compositions may include 100 mg nirogacestat or a pharmaceutically acceptable salt thereof and be administered once daily. In other examples, the compositions may include 100 mg nirogacestat or a pharmaceutically acceptable salt thereof and be administered twice daily. In other examples, the compositions may include 150 mg nirogacestat or a pharmaceutically acceptable salt thereof and be administered once daily. In other examples, the compositions may include 150 mg nirogacestat or a pharmaceutically acceptable salt thereof and be administered twice daily.

One embodiment is a solid oral pharmaceutical composition (such as a tablet or capsule) containing 50 mg (free base equivalent dose) of nirogacestat or a pharmaceutically acceptable salt thereof (such as nirogacestat dihydrobromide) which provides upon initial oral administration to a human subject a $C_{max}$ of less than 200 ng/ml (such as less than 190 ng/ml). In one embodiment, the solid pharmaceutical composition provides upon initial oral administration to the human subject a $C_{max}$ of from about 100 to about 200 ng/mL.

Another embodiment is a solid oral pharmaceutical composition (such as a tablet or capsule) containing 50 mg (free base equivalent dose) of nirogacestat or a pharmaceutically acceptable salt thereof (such as nirogacestat dihydrobromide) which provides upon initial oral administration to a human subject an $AUC_{last}$ of less than 725 ng·h/mL. In one embodiment, the solid oral pharmaceutical composition exhibits upon initial oral administration to the human subject a $C_{max}$ of less than 200 ng/ml (such as less than 190 ng/ml, or from about 100 to about 200 ng/ml).

Yet another embodiment is a solid oral pharmaceutical composition (such as a tablet or capsule) containing 50 mg (free base equivalent dose) of nirogacestat or a pharmaceutically acceptable salt thereof (such as nirogacestat dihydrobromide) which provides upon initial oral administration to a human subject an $AUC_{last}$ of from about 375 to about 725 ng·h/mL. In one embodiment, the solid oral pharmaceutical composition exhibits upon initial oral administration to the human subject a $C_{max}$ of less than 200 ng/ml (such as less than 190 ng/ml, or from about 100 to about 200 ng/ml).

Yet another embodiment is a solid oral pharmaceutical composition (such as a tablet or capsule) containing 50 mg (free base equivalent dose) of nirogacestat or a pharmaceutically acceptable salt thereof (such as nirogacestat dihydrobromide) which provides upon initial oral administration to a human subject an $AUC_{inf}$ of less than 725 ng·h/mL. In one embodiment, the solid oral pharmaceutical composition exhibits upon initial oral administration to the human subject a $C_{max}$ of less than 200 ng/mL (such as less than 190 ng/mL, or from about 100 to about 200 ng/ml).

Yet another embodiment is a solid oral pharmaceutical composition (such as a tablet or capsule) containing 50 mg (free base equivalent dose) of nirogacestat or a pharmaceutically acceptable salt thereof (such as nirogacestat dihydrobromide) which provides upon initial oral administration to a human subject an $AUC_{inf}$ of from about 375 to about 725 ng·h/mL. In one embodiment, the solid oral pharmaceutical composition exhibits upon initial oral administration to the human subject a $C_{max}$ of less than 200 ng/mL (such as less than 190 ng/ml, or from about 100 to about 200 ng/ml).

One embodiment is a solid oral pharmaceutical composition (such as a tablet or capsule) containing 100 mg (free base equivalent dose) of nirogacestat or a pharmaceutically acceptable salt thereof (such as nirogacestat dihydrobromide) which provides upon initial oral administration to a human subject a $C_{max}$ of less than 600 ng/ml (such as less than 570 ng/ml, or from about 300 to about 570 ng/mL).

Another embodiment is a solid oral pharmaceutical composition (such as a tablet or capsule) containing 100 mg (free base equivalent dose) of nirogacestat or a pharmaceutically acceptable salt thereof (such as nirogacestat dihydrobromide) which provides upon initial oral administration to a human subject an $AUC_{last}$ of less than 2300 ng·h/mL. In one embodiment, the solid oral pharmaceutical composition exhibits upon initial oral administration to the human subject a $C_{max}$ of less than 600 ng/ml (such as less than 570 ng/ml, or from about 300 to about 570 ng/ml).

Yet another embodiment is a solid oral pharmaceutical composition (such as a tablet or capsule) containing 100 mg (free base equivalent dose) of nirogacestat or a pharmaceutically acceptable salt thereof (such as nirogacestat dihydrobromide) which provides upon initial oral administration to a human subject an $AUC_{last}$ of from about 1200 to about 2300 ng·h/mL. In one embodiment, the solid oral pharmaceutical composition exhibits upon initial oral administration to the human subject a $C_{max}$ of less than 600 ng/ml (such as less than 570 ng/ml, or from about 300 to about 570 ng/ml).

Another embodiment is a solid oral pharmaceutical composition (such as a tablet or capsule) containing 100 mg (free base equivalent dose) of nirogacestat or a pharmaceutically acceptable salt thereof (such as nirogacestat dihydrobromide) which provides upon initial oral administration to a human subject an $AUC_{inf}$ of less than 2300 ng·h/mL. In one embodiment, the solid oral pharmaceutical composition exhibits upon initial oral administration to the human subject a $C_{max}$ of less than 600 ng/ml (such as less than 570 ng/ml, or from about 300 to about 570 ng/ml).

Yet another embodiment is a solid oral pharmaceutical composition (such as a tablet or capsule) containing 100 mg (free base equivalent dose) of nirogacestat or a pharmaceutically acceptable salt thereof (such as nirogacestat dihydrobromide) which provides upon initial oral administration to a human subject an $AUC_{inf}$ of from about 1200 to about 2300 ng·h/mL. In one embodiment, the solid oral pharmaceutical composition exhibits upon initial oral administration to the human subject a $C_{max}$ of less than 600 ng/ml (such as less than 570 ng/ml, or from about 300 to about 570 ng/ml).

One embodiment is a solid oral pharmaceutical composition (such as a tablet or capsule) containing 150 mg (free base equivalent dose) of nirogacestat or a pharmaceutically acceptable salt thereof (such as nirogacestat dihydrobromide) which provides upon initial oral administration to a human subject a $C_{max}$ of less than 1000 ng/ml (such as less than 950 ng/ml, or from about 480 to about 950 ng/ml).

Another embodiment is a solid oral pharmaceutical composition (such as a tablet or capsule) containing 150 mg (free base equivalent dose) of nirogacestat or a pharmaceutically acceptable salt thereof (such as nirogacestat dihydrobromide) which provides upon initial oral administration to a human subject an $AUC_{last}$ of less than 4000 ng·h/mL. In one embodiment, the solid oral pharmaceutical composition exhibits upon initial oral administration to the human subject a $C_{max}$ of less than 1000 ng/ml (such as less than 950 ng/ml, or from about 480 to about 950 ng/mL).

Yet another embodiment is a solid oral pharmaceutical composition (such as a tablet or capsule) containing 150 mg (free base equivalent dose) of nirogacestat or a pharmaceutically acceptable salt thereof (such as nirogacestat dihydrobromide) which provides upon initial oral administration to a human subject an $AUC_{last}$ of from about 2000 to about 4000 ng·h/mL. In one embodiment, the solid oral pharmaceutical composition exhibits upon initial oral administration to the human subject a $C_{max}$ of less than 1000 ng/ml (such as less than 950 ng/ml, or from about 480 to about 950 ng/ml).

Another embodiment is a solid oral pharmaceutical composition (such as a tablet or capsule) containing 150 mg (free base equivalent dose) of nirogacestat or a pharmaceutically acceptable salt thereof (such as nirogacestat dihydrobromide) which provides upon initial oral administration to a human subject an $AUC_{inf}$ of less than 4000 ng·h/mL. In one embodiment, the solid oral pharmaceutical composition exhibits upon initial oral administration to the human subject a $C_{max}$ of less than 1000 ng/ml (such as less than 950 ng/ml, or from about 480 to about 950 ng/ml).

Yet another embodiment is a solid oral pharmaceutical composition (such as a tablet or capsule) containing 150 mg (free base equivalent dose) of nirogacestat or a pharmaceutically acceptable salt thereof (such as nirogacestat dihydrobromide) which provides upon initial oral administration to a human subject an $AUC_{inf}$ of from about 2000 to about 4000 ng·h/mL. In one embodiment, the solid oral pharmaceutical composition exhibits upon initial oral administration to the human subject a $C_{max}$ of less than 1000 ng/ml (such as less than 950 ng/mL, or from about 480 to about 950 ng/mL).

III. Methods of Treatment

A. Ovarian Cancer

In some embodiments, nirogacestat can be administered to a patient to treat ovarian cancer. In some instances, the ovarian cancer is epithelial ovarian cancer. In some instances, the epithelial ovarian cancer is a serous carcinoma. In some instances, the epithelial ovarian cancer is a endometrioid carcinoma. In some instances, the epithelial ovarian cancer is a mucinous carcinoma. In some instances, the epithelial ovarian cancer is a clear cell carcinoma. In some instances, the ovarian cancer is germ cell ovarian tumor. In some instances, the germ cell ovarian tumor is a teratoma. In some instances, the germ cell ovarian tumor is a dysgerminoma. In some instances, the germ cell tumor is a endodermal sinus tumor. In some instances, the ovarian germ cell tumor is a choriocarcinoma tumor. In some instances, the ovarian cancer is ovarian sarcoma. In some instances, the ovarian cancer is a krukenberg tumor. In some instances, the ovarian cancer is a small cell carcinoma (SCCO). In some instances the ovarian cancer is a stromal cell ovarian cancer. In some instances, the ovarian cancer is a Sertoli-Leydig Cell tumor. In some instances, the ovarian cancer is ovarian carcinosarcoma. In some instances, the ovarian cancer is ovarian sex cord stromal tumors (SCSTs). In some instances, the ovarian cancer is ovarian granulosa cell tumors (OvGCT). In some in instances, the ovarian cancer is borderline ovarian tumors. In some embodiments, the ovarian cancer is stromal cell tumors.

Nirogacestat can be administered to a patient to treat ovarian cancer. In some aspects, the methods for treating ovarian cancer in a patient in need thereof comprise administering to the patient an oral dosage of nirogacestat or a pharmaceutically acceptable salt thereof (e.g., dihydrobromide salt form) wherein the oral dosage provides a mean maximum drug plasma concentration ($C_{max}$) of more than 100 ng/ml. In some aspects, the methods for treating ovarian cancer in a patient in need thereof comprise administering to the patient an oral dosage of nirogacestat or a pharmaceutically acceptable salt thereof (e.g., dihydrobromide salt form) wherein the oral dosage provides a mean maximum drug plasma concentration ($C_{max}$) of about 150 ng/ml to about 500 ng/ml. In some aspects, the methods for treating ovarian cancer in a patient in need thereof comprises administering to the patient an oral dosage of nirogacestat or a pharmaceutically acceptable salt thereof (e.g., dihydrobromide salt form) wherein the oral dosage provides a mean maximum drug plasma concentration ($C_{max}$) of about 200 ng/ml to about 500 ng/ml. In some aspects, the methods for treating ovarian cancer in a patient in need thereof comprise administering to the patient an oral dosage of nirogacestat or a pharmaceutically acceptable salt thereof (e.g., dihydrobromide salt form) wherein the oral dosage provides a mean maximum drug plasma concentration ($C_{max}$) of about 250 ng/ml to about 500 ng/ml. In some aspects, the methods for treating ovarian cancer in a patient in need thereof comprise administering to the patient an oral dosage of nirogacestat or a pharmaceutically acceptable salt thereof (e.g., dihydrobromide salt form) wherein the oral dosage provides a mean maximum drug plasma concentration ($C_{max}$) of about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/1, about 425 ng/ml, about 450 ng/ml, about 475 ng/ml, or about 500 ng/ml.

In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of less than 700 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 200 ng·h/ml to about 650 ng·h/ml. In some aspects, the methods for treating ovarian cancer in a patient in need thereof comprise administering to the patient an mg oral dosage of nirogacestat or a pharmaceutically acceptable salt thereof (e.g., a dihydrobromide salt form) wherein the oral dosage provides an in vivo area under the plasma curve ($AUC_{inf}$) of about 250 ng·h/ml to about 650 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 300 ng·h/ml to about 650 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 200 ng·h/ml, about 225 ng·h/ml, about 250 ng·h/ml, about 275 ng·h/ml, about 300 ng·h/ml, about 325 ng·h/ml, about 350 ng·h/ml, about 375 ng·h/ml, about 400 ng·h/ml, about 425 ng·h/ml, about 450 ng·h/ml, about 475 ng·h/ml, about 500 ng·h/ml, about 525 ng·h/ml, about 550 ng·h/ml, about 575 g h/ml, about 600 ng·h/ml, about 625 ng·h/ml, or about 675 ng·h/ml.

In some aspects, the methods for treating ovarian cancer comprise administration to a patient in need thereof an oral dosage form comprising 50 mg of nirogacestat or a pharmaceutically acceptable salt thereof (e.g., a dihydrobromide salt form) to a patient in need thereof.

In some aspects, the methods for treating ovarian cancer in a patient in need thereof comprise administering to the patient a 50 mg oral dosage of nirogacestat or a pharmaceutically acceptable salt thereof (e.g., dihydrobromide salt form) wherein the oral dosage provides a mean maximum drug plasma concentration ($C_{max}$) of more than 100 ng/ml. In some aspects, the methods for treating ovarian cancer in a patient in need thereof comprise administering to the patient a 50 mg oral dosage of nirogacestat or a pharmaceutically acceptable salt thereof (e.g., dihydrobromide salt form) wherein the oral dosage provides a mean maximum drug plasma concentration ($C_{max}$) of about 150 ng/ml to about 500 ng/ml. In some aspects, the methods for treating ovarian cancer in a patient in need thereof comprise administering to the patient a 50 mg oral dosage of nirogacestat or a pharmaceutically acceptable salt thereof (e.g., dihydrobromide salt form) wherein the oral dosage provides a mean maximum drug plasma concentration ($C_{max}$) of about 200 ng/ml to about 500 ng/ml. In some aspects, the methods for treating ovarian cancer in a patient in need thereof comprise administering to the patient a 50 mg oral dosage of nirogacestat or a pharmaceutically acceptable salt thereof (e.g., dihydrobromide salt form) wherein the oral dosage provides a mean maximum drug plasma concentration ($C_{max}$) of about 250 ng/ml to about 500 ng/ml. In some aspects, the methods for treating ovarian cancer in a patient in need thereof comprise administering to the patient a 50 mg oral dosage of nirogacestat or a pharmaceutically acceptable salt thereof (e.g., dihydrobromide salt form) wherein the oral dosage provides a mean maximum drug plasma concentration ($C_{max}$) of about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/l, about 425 ng/ml, about 450 ng/ml, about 475 ng/ml, or about 500 ng/ml.

In some aspects, the methods for treating ovarian cancer in a patient in need thereof comprise administering to the patient a 50 mg oral dosage of nirogacestat or a pharmaceutically acceptable salt thereof (e.g., a dihydrobromide salt form) wherein the oral dosage provides an in vivo area under the plasma curve ($AUC_{inf}$) of less than 700 ng·h/ml. In some aspects, the methods for treating ovarian cancer in a patient in need thereof comprise administering to the patient a 50 mg oral dosage of nirogacestat or a pharmaceutically acceptable salt thereof (e.g., a dihydrobromide salt form) wherein the oral dosage provides an in vivo area under the plasma curve ($AUC_{inf}$) of about 200 ng·h/ml to about 650 ng·h/ml. In some aspects, the methods for treating ovarian cancer in a patient in need thereof comprise administering to the patient a 50 mg oral dosage of nirogacestat or a pharmaceutically acceptable salt thereof (e.g., a dihydrobromide salt form) wherein the oral dosage provides an in vivo area under the plasma curve ($AUC_{inf}$) of about 250 ng·h/ml to about 650 ng·h/ml. In some aspects, the methods for treating ovarian cancer in a patient in need thereof comprise administering to the patient a 50 mg oral dosage of nirogacestat or a pharmaceutically acceptable salt thereof (e.g., a dihydrobromide salt form) wherein the oral dosage provides an in vivo area under the plasma curve ($AUC_{inf}$) of about 300 ng·h/ml to about 650 ng·h/ml. In some aspects, the methods for treating ovarian cancer in a patient in need thereof comprise administering to the patient a 50 mg oral dosage of nirogacestat or a pharmaceutically acceptable salt thereof (e.g., a dihydrobromide salt form) wherein the oral dosage provides an in vivo area under the plasma curve ($AUC_{inf}$) of about 200 ng·h/ml, about 225 ng·h/ml, about 250 ng·h/ml, about 275 ng·h/ml, about 300 ng·h/ml, about 325 ng·h/ml, about 350 ng·h/ml, about 375 ng. h/ml, about 400 ng·h/ml, about 425 ng·h/ml, about 450 ng·h/ml, about 475 ng·h/ml, about 500 ng·h/ml, about 525 ng·h/ml, about 550 ng·h/ml, about 575 g h/ml, about 600 ng·h/ml, about 625 ng·h/ml, or about 675 ng·h/ml.

In some aspects, the methods for treating ovarian cancer in a patient in need thereof comprise administering to the patient 300 mg per day of nirogacestat or a pharmaceutically acceptable salt thereof (e.g., a dihydrobromide salt form).

In some aspects, the methods for treating ovarian cancer comprise orally administering the nirogacestat or a pharmaceutically acceptable salt thereof (e.g., a dihydrobromide salt form). In some aspects, the methods for treating ovarian cancer comprise orally administering the nirogacestat or a pharmaceutically acceptable salt thereof (e.g., a dihydrobromide salt form) as a solid dosage form. In some aspects, the solid dosage forms are tablets or capsules.

In some aspects, the methods for treating ovarian cancer comprise administering the nirogacestat or pharmaceutically acceptable salt thereof (e.g., a dihydrobromide salt form) once daily. In some aspects, the methods for treating ovarian cancer comprise administering the nirogacestat or pharmaceutically acceptable salt thereof (e.g., a dihydrobromide salt form) two, three, or four times daily. If the nirogacestat or pharmaceutically acceptable salt thereof (e.g., a dihydrobromide salt form) is administered more than one times daily, the total daily dose administered each time can be the same or different. For example, if 300 mg nirogacestat or pharmaceutically acceptable salt thereof (e.g., a dihydrobromide salt form) is to be administered two times daily, the patient could receive either two 150 mg doses (e.g., one 150 mg dose at 8 am and one 150 mg dose at 8 pm) or a 100 mg dose in the morning and a 200 mg dose in the evening. Each dose can also consist of more than one solid dosage form. For example, a 150 mg individual dose (i.e., the morning dose of a 300 mg total daily dose to be administered as two separate doses) could be administered as three 50 mg tablets.

In one embodiment, the patient having ovarian cancer is treated with 150 mg nirogacestat twice daily (for a total daily dose of 300 mg nirogacestat). In a preferred embodiment, the nirogacestat is administered in the form of its dihydrobromide salt. In one preferred embodiment, the dose is modified upon due to adverse reactions as follows:

In one embodiment, the dose is modified for selected severe adverse reactions as described in Table 1 below. All adverse reactions or events are graded according to the U.S. National Cancer Institute's Common Terminology Criteria for Adverse Events (CTCAE), version 5.0, which is hereby incorporated by reference. For adverse events (or adverse reactions) or severe adverse events not listed in the CTCAE, the following grading system was used: Grade 1 refers to mild; asymptomatic or mild symptoms; clinical or diagnostic observations only; treatment not indicated. Grade 3 refer to severe or medically significant but not immediately life-threatening; hospitalization or prolongation of hospitalization indicated; disabling; limiting self-care activities of daily living. Self-care activities of daily living refers to bathing, dressing and undressing, feeding self, using the toilet, taking medications, and not bedridden.

TABLE 1

Dose Modifications for Adverse Reactions

| Adverse Reaction | Intervention |
|---|---|
| Diarrhea | |
| Grade 3 diarrhea persisting for ≥3 days despite maximal medical therapy | Withhold drug (nirogacestat or a pharmaceutically acceptable salt thereof) until resolved to Grade ≤1 or baseline, then restart at a dose of 100 mg twice daily. |
| Skin Reactions | |
| Grade 3 folliculitis | Withhold drug until resolved to Grade ≤1 or baseline, then restart at a dose of 100 mg twice daily. |
| Grade 3 maculopapular rash | Withhold drug until resolved to Grade ≤1 or baseline, then restart at a dose of 100 mg twice daily. |
| Grade 3 hidradenitis | Withhold drug until resolved to Grade ≤1 or baseline, then restart at a dose of 100 mg twice daily. |
| Electrolyte Abnormalities | |
| Grade 3 hypophosphatemia persisting for ≥7 days despite maximal replacement therapy | Withhold drug until resolved to Grade ≤1 or baseline, then restart at a dose of 100 mg twice daily. |
| Grade 3 hypokalemia despite maximal replacement therapy | Withhold drug until resolved to Grade ≤1 or baseline, then restart at a dose of 100 mg twice daily. |
| Elevated Liver Transaminases | |
| ALT or AST ≥3 to 5 × ULN | Withhold drug until ALT, AST, or both are resolved to <3 × ULN or baseline, then restart at a dose of 100 mg twice daily |
| ALT or AST >5 × ULN | Permanently discontinue |
| Other Adverse Reactions | |
| Anaphylaxis or other severe hypersensitivity reaction | Permanently discontinue |

ALT=alanine transaminase; AST=aspartate aminotransferase; ULN=upper limit of normal In a further embodiment, for severe adverse reactions other than those in Table 1, or in the event of life-threatening adverse reactions, the nirogacestat is withheld until the reaction is resolved to Grade≤1 or baseline. Treatment with nirogacestat may be restarted at a dose of 100 mg twice daily after consideration of the potential benefit and likelihood of recurrence of the adverse reaction. Nirogacestat is permanently discontinued upon recurrence of a severe or life-threatening adverse reaction upon rechallenge at the reduced dose (i.e., 100 mg twice daily).

In some aspects, the methods for treating ovarian cancer in a patient in need thereof comprise administering to the patient an oral dosage of nirogacestat or a pharmaceutically acceptable salt thereof (e.g., dihydrobromide salt form) wherein the oral dosage provides a mean maximum drug plasma concentration ($C_{max}$) of more than 225 ng/ml. In some aspects, the methods for treating ovarian cancer in a patient in need thereof comprise administering to the patient an oral dosage of nirogacestat or a pharmaceutically acceptable salt thereof (e.g., dihydrobromide salt form) wherein the oral dosage provides a mean maximum drug plasma concentration ($C_{max}$) of about 250 ng/ml to about 750 ng/ml. In some aspects, the methods for treating ovarian cancer in a patient in need thereof comprise administering to the patient an oral dosage of nirogacestat or a pharmaceutically acceptable salt thereof (e.g., dihydrobromide salt form) wherein the oral dosage provides a mean maximum drug plasma concentration ($C_{max}$) of about 300 ng/ml to about 750 ng/ml. In some aspects, the methods for treating ovarian cancer in a patient in need thereof comprise administering to the patient an oral dosage of nirogacestat or a pharmaceutically acceptable salt thereof (e.g., dihydrobromide salt form) wherein the oral dosage provides a mean maximum drug plasma concentration ($C_{max}$) of about 350 ng/ml to about 750 ng/ml. In some aspects, the methods for treating ovarian cancer in a patient in need thereof comprise administering to the patient an oral dosage of nirogacestat or a pharmaceutically acceptable salt thereof (e.g., dihydrobromide salt form) wherein the oral dosage provides a mean maximum drug plasma concentration ($C_{max}$) of about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/l, about 550 ng/ml, about 575 ng/ml, about 600 ng/ml, about 625 ng/ml, about 650 ng/ml, about 675 ng/ml, about 700 ng/ml, about 725 ng/ml, or about 750 ng/ml.

In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of less than 3000 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 200 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 250 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 300 ng. h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 350 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 400 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 450 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 500 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 550 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 600 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 650 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 700 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 750 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 800 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 850 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 900 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 950 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1000 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1050 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1100 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1150 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1200 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1250 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1350 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1400 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1450 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1500 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1550 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1600 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1650 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1700 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1750 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1800 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1850 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1900 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 1950 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2000 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2050 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2100 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2150 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2200 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2250 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2300 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2350 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2400 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2450 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2500 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2550 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2600 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2650 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2700 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 2750 ng·h/ml to about 2950 ng·h/ml. In some aspects, the methods for treating ovarian cancer in a patient in need thereof comprise administering to the patient an oral dosage of nirogacestat or a pharmaceutically acceptable salt thereof (e.g., a dihydrobromide salt form) wherein the oral dosage provides an in vivo area under the plasma curve ($AUC_{inf}$) of about 200 ng·h/ml, about 225 ng·h/ml, about 250 ng·h/ml, about 275 ng·h/ml, about 300 ng·h/ml, about 325 ng·h/ml, about 350 ng·h/ml, about 375 ng·h/ml, about 400 ng·h/ml, about 425 ng·h/ml, about 450 ng·h/ml, about 475 ng·h/ml, about 500 ng·h/ml, about 525 ng·h/ml, about 550 ng·h/ml, about 575 g h/ml, about 600 ng·h/ml, about 625 ng·h/ml, about 675 ng·h/ml, about 700 ng·h/ml, about 725 ng·h/ml, about 750 ng·h/ml, about 775 ng·h/ml, about 800 ng·h/ml, about 825 ng·h/ml, about 850 ng·h/ml, about 875 ng·h/ml, about 900 ng·h/ml, about 925 ng·h/ml, about 950 ng·h/ml, about 975 ng·h/ml, about 1000 ng·h/ml, about 1025 ng·h/ml, about 1050 ng·h/ml, about 1075 ng·h/ml, about 1100 ng·h/ml, about 1125 ng·h/ml, about 1150 ng·h/ml, about 1175 ng·h/ml, about 1200 ng·h/ml, about 1225 ng·h/ml, about 1250 ng·h/ml, about 1275 ng·h/ml, about 1300 ng·h/ml, about 1325 ng·h/ml, about 1350 ng·h/ml, about 1375 ng·h/ml, about 1400 ng·h/ml, about 1425 ng·h/ml, about 1450 ng·h/ml, about 1475 ng·h/ml, about 1500 ng·h/ml, about 1525 ng·h/ml, about 1550 ng·h/ml, about 1575 ng·h/ml, about 1600 ng·h/ml, about 1625 ng·h/ml, about 1650 ng·h/ml, about 1675 ng·h/ml, about 1700 ng·h/ml, about 1725 ng·h/ml, about 1750 ng·h/ml, about 1775 ng·h/ml, about 1800 ng·h/ml, about 1825 ng·h/ml, about 1850 ng·h/ml, about 1875 ng·h/ml, about 1900 ng·h/ml, about 1925 ng·h/ml, about 1950 ng·h/ml, about 2000 ng·h/ml, about 2025 ng·h/ml, about 2050 ng·h/ml, about 2100 ng·h/ml, about 2125 ng·h/ml, about 2150 ng·h/ml, about 2175 ng·h/ml, about 2200 ng·h/ml, about 2225 ng·h/ml, about 2250 ng·h/ml, about 2275 ng·h/ml, about 2300 ng·h/ml, about 2325 ng·h/ml, about 2550 ng·h/ml, about 2575 ng·h/ml, about 2600 ng·h/ml, about 2625 ng·h/ml, about 2650 ng·h/ml, about 2675 ng·h/ml, about 2700 ng·h/ml, about 2725 ng·h/ml, about 2750 ng·h/ml, about 2775 ng·h/ml, about 2800 ng·h/ml, about 2825 ng·h/ml, about 2850 ng·h/ml, about 2875 ng·h/ml, about 2900 ng·h/ml, about 2925 ng·h/ml, or about 2950 ng·h/ml.

In some aspects, the methods for treating ovarian cancer comprise administration to a patient in need thereof 200 mg per day of nirogacestat or a pharmaceutically acceptable salt thereof (e.g., a dihydrobromide salt form). For example, the method may include administering 100 mg twice daily of nirogacestat or a pharmaceutically acceptable salt thereof (e.g., a dihydrobromide salt form). In some aspects, the methods for treating ovarian cancer comprise administration to a patient in need thereof 100 mg per day of nirogacestat or a pharmaceutically acceptable salt thereof (e.g., a dihydrobromide salt form). In some aspects, the methods for treating ovarian cancer comprise administration to a patient in need thereof 100 mg per day of nirogacestat or a pharmaceutically acceptable salt thereof (e.g., a dihydrobromide salt form). In some aspects, the methods for treating ovarian cancer comprise administration to a patient in need thereof 50 mg per day of nirogacestat or a pharmaceutically acceptable salt thereof (e.g., a dihydrobromide salt form)

In some aspects, the methods for treating ovarian cancer in a patient in need thereof comprise administering to the patient a 50 mg oral dosage of nirogacestat or a pharmaceutically acceptable salt thereof (e.g., dihydrobromide salt form) wherein the oral dosage provides a mean maximum drug plasma concentration ($C_{max}$) of more than 100 ng/ml. In some aspects, the methods for treating ovarian cancer in a patient in need thereof comprise administering to the patient a 50 mg oral dosage of nirogacestat or a pharmaceutically acceptable salt thereof (e.g., dihydrobromide salt form) wherein the oral dosage provides a mean maximum drug plasma concentration ($C_{max}$) of about 150 ng/ml to about 500 ng/ml. In some aspects, the methods for treating ovarian cancer in a patient in need thereof comprise administering to the patient a 50 mg oral dosage of nirogacestat or a pharmaceutically acceptable salt thereof (e.g., dihydrobromide salt form) wherein the oral dosage provides a mean maximum drug plasma concentration ($C_{max}$) of about 200 ng/ml to about 500 ng/ml. In some aspects, the methods for treating ovarian cancer in a patient in need thereof comprise administering to the patient a 50 mg oral dosage of nirogacestat or a pharmaceutically acceptable salt thereof (e.g., dihydrobromide salt form) wherein the oral dosage provides a mean maximum drug plasma concentration ($C_{max}$) of about 250 ng/ml to about 500 ng/ml. In some aspects, the methods for treating ovarian cancer in a patient in need thereof comprise administering to the patient a 50 mg oral dosage of nirogacestat or a pharmaceutically acceptable salt thereof (e.g., dihydrobromide salt form) wherein the oral dosage provides a mean maximum drug plasma concentration ($C_{max}$) of about 125 ng/ml, about 150 ng/ml, about 175 ng/ml, about 200 ng/ml, about 225 ng/ml, about 250 ng/ml, about 275 ng/ml, about 300 ng/ml, about 325 ng/ml, about 350 ng/ml, about 375 ng/ml, about 400 ng/l, about 425 ng/ml, about 450 ng/ml, about 475 ng/ml, or about 500 ng/ml.

In some aspects, the methods for treating ovarian cancer in a patient in need thereof comprise administering to the patient a 100 mg oral dosage of nirogacestat or a pharmaceutically acceptable salt thereof (e.g., dihydrobromide salt form) wherein the oral dosage provides a mean maximum drug plasma concentration ($C_{max}$) of more than 225 ng/ml. In some aspects, the methods for treating ovarian cancer in a patient in need thereof comprise administering to the patient a 100 mg oral dosage of nirogacestat or a pharmaceutically acceptable salt thereof (e.g., dihydrobromide salt form) wherein the oral dosage provides a mean maximum drug plasma concentration ($C_{max}$) of about 250 ng/ml to about 750 ng/ml. In some aspects, the methods for treating ovarian cancer in a patient in need thereof comprise administering to the patient a 100 mg oral dosage of nirogacestat or a pharmaceutically acceptable salt thereof (e.g., dihydrobromide salt form) wherein the oral dosage provides a mean maximum drug plasma concentration ($C_{max}$) of about 300 ng/ml to about 750 ng/ml. In some aspects, the methods for treating ovarian cancer in a patient in need thereof comprise administering to the patient a 100 mg oral dosage of nirogacestat or a pharmaceutically acceptable salt thereof (e.g., dihydrobromide salt form) wherein the oral dosage provides a mean maximum drug plasma concentration ($C_{max}$) of about 350 ng/ml to about 750 ng/ml. In some aspects, the methods for treating ovarian cancer in a patient in need thereof comprise administering to the patient a 100 mg oral dosage of nirogacestat or a pharmaceutically acceptable salt thereof (e.g., dihydrobromide salt form) wherein the oral dosage provides a mean maximum drug plasma concentration ($C_{max}$) of about 250 ng/ml, about 275 ng/ml, about 300 ng/ml, about 325 ng/ml, about 350 ng/ml, about 375 ng/ml, about 400 ng/ml, about 425 ng/ml, about 450 ng/ml, about 475 ng/ml, about 500 ng/ml, about 525 ng/1, about 550 ng/ml, about 575 ng/ml, about 600 ng/ml, about 625 ng/ml, about 650 ng/ml, about 675 ng/ml, about 700 ng/ml, about 725 ng/ml, or about 750 ng/ml.

In some aspects, the methods for treating ovarian cancer in a patient in need thereof comprise administering to the patient a 50 mg oral dosage of nirogacestat or a pharmaceutically acceptable salt thereof (e.g., a dihydrobromide salt form) wherein the oral dosage provides an in vivo area under the plasma curve ($AUC_{inf}$) of less than 700 ng·h/ml. In some aspects, the methods for treating ovarian cancer in a patient in need thereof comprise administering to the patient a 50 mg oral dosage of nirogacestat or a pharmaceutically acceptable salt thereof (e.g., a dihydrobromide salt form) wherein the oral dosage provides an in vivo area under the plasma curve ($AUC_{inf}$) of about 200 ng·h/ml to about 650 ng·h/ml. In some aspects, the methods for treating ovarian cancer in a patient in need thereof comprise administering to the patient a 50 mg oral dosage of nirogacestat or a pharmaceutically acceptable salt thereof (e.g., a dihydrobromide salt form) wherein the oral dosage provides an in vivo area under the plasma curve ($AUC_{inf}$) of about 250 ng·h/ml to about 650 ng·h/ml. In some aspects, the methods for treating ovarian cancer in a patient in need thereof comprise administering to the patient a 50 mg oral dosage of nirogacestat or a pharmaceutically acceptable salt thereof (e.g., a dihydrobromide salt form) wherein the oral dosage provides an in vivo area under the plasma curve ($AUC_{inf}$) of about 300 ng·h/ml to about 650 ng·h/ml. In some aspects, the methods for treating ovarian cancer in a patient in need thereof comprise administering to the patient a 50 mg oral dosage of nirogacestat or a pharmaceutically acceptable salt thereof (e.g., a dihydrobromide salt form) wherein the oral dosage provides an in vivo area under the plasma curve ($AUC_{inf}$) of about 200 ng·h/ml, about 225 ng·h/ml, about 250 ng·h/ml, about 275 ng·h/ml, about 300 ng·h/ml, about 325 ng·h/ml, about 350 ng·h/ml, about 375 ng·h/ml, about 400 ng·h/ml, about 425 ng·h/ml, about 450 ng·h/ml, about 475 ng·h/ml, about 500 ng·h/ml, about 525 ng·h/ml, about 550 ng·h/ml, about 575 g h/ml, about 600 ng·h/ml, about 625 ng·h/ml, or about 675 ng·h/ml.

In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of less than 3000 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 200 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 250 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 300 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 350 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 400 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 450 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 500 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 550 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 600 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 650 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 700 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form)

wherein the oral dosage provides an in vivo area under the plasma curve ($AUC_{inf}$) of about 750 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 800 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 850 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 900 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 950 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1000 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1050 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1100 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1150 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1200 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1250 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1350 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1400 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1450 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1500 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1550 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1600 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1650 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1700 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1750 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1800 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1850 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1900 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 1950 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2000 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2050 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2100 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2150 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2200 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2250 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2300 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2350 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2400 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2450 ng. h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2500 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2550 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2600 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2650 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2700 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 2750 ng·h/ml to about 2950 ng·h/ml. In some aspects, the methods for treating ovarian cancer in a patient in need thereof comprise administering to the patient a 100 mg oral dosage of nirogacestat or a pharmaceutically acceptable salt thereof (e.g., a dihydrobromide salt form) wherein the oral dosage provides an in vivo area under the plasma curve ($AUC_{inf}$) of about 200 ng·h/ml, about 225 ng·h/ml, about 250 ng·h/ml, about 275 ng·h/ml, about 300 ng·h/ml, about 325 ng·h/ml, about 350 ng·h/ml, about 375 ng·h/ml, about 400 ng·h/ml, about 425 ng·h/ml, about 450 ng·h/ml, about 475 ng·h/ml, about 500 ng·h/ml, about 525 ng·h/ml, about 550 ng·h/ml, about 575 g h/ml, about 600 ng·h/ml, about 625 ng·h/ml, about 675 ng·h/ml, about 700 ng·h/ml, about 725 ng·h/ml, about 750 ng·h/ml, about 775 ng·h/ml, about 800 ng·h/ml, about 825 ng·h/ml, about 850 ng·h/ml, about 875 ng·h/ml, about 900 ng·h/ml, about 925 ng·h/ml, about 950 ng·h/ml, about 975 ng·h/ml, about 1000 ng·h/ml, about 1025 ng·h/ml, about 1050 ng·h/ml, about 1075 ng·h/ml, about 1100 ng·h/ml, about 1125 ng·h/ml, about 1150 ng·h/ml, about 1175 ng·h/ml, about 1200 ng·h/ml, about 1225 ng·h/ml, about 1250 ng·h/ml, about 1275 ng·h/ml, about 1300 ng·h/ml, about 1325 ng·h/ml, about 1350 ng·h/ml, about 1375 ng·h/ml, about 1400 ng·h/ml, about 1425 ng·h/ml, about 1450 ng·h/ml, about 1475 ng·h/ml, about 1500 ng·h/ml, about 1525 ng·h/ml, about 1550 ng·h/ml, about 1575 ng·h/ml, about 1600 ng·h/ml, about 1625 ng·h/ml, about 1650 ng·h/ml, about 1675 ng·h/ml, about 1700 ng·h/ml, about 1725 ng·h/ml, about 1750 ng·h/ml, about 1775 ng·h/ml, about 1800 ng·h/ml, about 1825 ng·h/ml, about 1850 ng·h/ml, about 1875 ng·h/ml, about 1900 ng·h/ml, about 1925 ng·h/ml, about 1950 ng·h/ml, about 2000 ng·h/ml, about 2025 ng·h/ml, about 2050 ng·h/ml, about 2100 ng·h/ml, about 2125 ng·h/ml, about 2150 ng·h/ml, about 2175 ng. h/ml, about 2200 ng·h/ml, about 2225 ng·h/ml, about 2250 ng·h/ml, about 2275 ng. h/ml, about 2300 ng·h/ml, about 2325 ng·h/ml, about 2550 ng·h/ml, about 2575 ng·h/ml, about 2600 ng·h/ml, about 2625 ng. h/ml, about 2650 ng·h/ml, about 2675 ng·h/ml, about 2700 ng·h/ml, about 2725 ng·h/ml, about 2750 ng·h/ml, about 2775 ng·h/ml, about 2800 ng. h/ml, about 2825 ng·h/ml, about 2850 ng·h/ml, about 2875 ng. h/ml, about 2900 ng·h/ml, about 2925 ng·h/ml, or about 2950 ng·h/ml.

In some aspects, the methods for treating ovarian cancer comprise orally administering the nirogacestat or a pharmaceutically acceptable salt thereof (e.g., a dihydrobromide salt form). In some aspects, the methods for treating ovarian cancer comprise orally administering the nirogacestat or a pharmaceutically acceptable salt thereof (e.g., a dihydrobromide salt form) as a solid dosage form. In some aspects, the solid dosage form is a tablet or capsule.

In some aspects, the methods for treating ovarian cancer comprise administering nirogacestat or pharmaceutically acceptable salt thereof (e.g., a dihydrobromide salt form) once daily. In some aspects, the methods for treating ovarian cancer comprise administering nirogacestat or pharmaceutically acceptable salt thereof (e.g., a dihydrobromide salt form) twice daily. In some aspects, the methods for treating ovarian cancer comprise administering the nirogacestat or pharmaceutically acceptable salt thereof (e.g., a dihydrobromide salt form) two, three, or four times daily. If the nirogacestat or pharmaceutically acceptable salt thereof (e.g., a dihydrobromide salt form) is administered more than one times daily, the total daily dose administered each time can be the same or different. For example, if 100 mg nirogacestat or pharmaceutically acceptable salt thereof (e.g., a dihydrobromide salt form) is to be administered two times daily, the patient could receive either two 50 mg doses (e.g., one 50 mg dose at 8 am and one 50 mg dose at 8 pm) or a 25 mg dose in the morning and a 75 mg dose in the evening. Each dose can also consist of more than one solid dosage form. For example, a 50 mg individual dose (i.e., the morning dose of a 100 mg total daily dose to be administered as two separate doses) could be administered as two 25 mg tablets.

In some aspects, the methods for treating ovarian cancer comprise administering a single oral dosage of nirogacestat or pharmaceutically acceptable salt thereof (e.g., a dihydrobromide salt form) for the concomitant treatment of ovarian cancer. In a concomitant therapy for treatment of ovarian cancer, the nirogacestat or pharmaceutically acceptable salt thereof (e.g., a dihydrobromide salt form) is administered with one or more additional active ingredients. In some aspects, the concomitant therapy for the treatment of ovarian cancer comprises administering the nirogacestat or pharmaceutically acceptable salt thereof (e.g., a dihydrobromide salt form) in combination with BCMA-therapy. In some aspects, the BCMA-directed therapy includes one or more of an allogeneic chimeric antigen receptor T cell therapy, an autologous chimeric antigen receptor T cell therapy, an immunotherapy (e.g., a monoclonal antibody therapy), an antibody drug conjugate therapy, or a bispecific antibody therapy with dual specificity for BCMA and an immune-related target (e.g., CD3). In other aspects, the BCMA-directed therapy includes at least an allogeneic chimeric antigen receptor T cell therapy. In other aspects, the BCMA-directed therapy includes at least an autologous chimeric antigen receptor T cell therapy. In another aspect, the BCMA-directed therapy includes at least an immunotherapy (e.g., a monoclonal antibody therapy). In other aspects, the BCMA-directed therapy includes at least an antibody drug conjugate therapy. In other aspects, the BCMA-directed therapy includes at least a bispecific antibody therapy with dual specificity for BCMA and an immune-related target (e.g., CD3). In some aspects, the methods for treating ovarian cancer comprise administering to the patient an oral dosage of nirogacestat or a pharmaceutically acceptable salt thereof in combination with belantamab mafodotin.

In the concomitant therapy (e.g., in combination with belantamab mafodotin) for treatment of ovarian cancer, the nirogacestat or pharmaceutically acceptable salt thereof (e.g., a dihydrobromide salt form) is administered to the subject before, simultaneously, or subsequently to the other active ingredient(s) (e.g., belantamab mafodotin).

In some aspects, treating ovarian cancer comprises administering the concomitant therapy of nirogacestat or pharmaceutically acceptable salt thereof (e.g., a dihydrobromide salt form) and other active ingredient(s) (e.g., belantamab mafodotin) as a first line therapy. In such aspect, the patient having, ovarian cancer can have previously received and/or be currently being treated for one or more unrelated diseases or disorders (e.g., anxiety).

In some aspects, treating ovarian cancer comprises administering nirogacestat or a pharmaceutically acceptable salt thereof (e.g., a dihydrobromide salt form) and a BCMA-directed therapy (e.g., belantamab mafodotin) to a patient that has been previously treated for the ovarian cancer. In some aspects, the patient with ovarian cancer has been previously treated for the ovarian cancer with one or more of a proteasome inhibitor, an immunomodulatory therapy, an immunotherapy (e.g., a monoclonal antibody, such as a monoclonal antibody directed to CD38), a stem cell transplant, a chemotherapy, a targeted therapy (e.g., an XPO1 inhibitor), or a BCMA-directed therapy not in combination with nirogacestat.

In one aspect, the nirogacestat or pharmaceutically acceptable salt thereof (e.g., a dihydrobromide salt form) is administered orally and the BCMA-directed therapy (e.g., belantamab mafodotin) is administered intravenously or subcutaneously to the subject.

In some aspects, the patient with ovarian cancer exhibits a complete response following administration of the nirogacestat or pharmaceutically acceptable salt thereof (e.g., a dihydrobromide salt form) and BCMA-directed therapy (e.g., belantamab mafodotin). In some aspects, the patient with ovarian cancer exhibits a near complete response following administration of the nirogacestat or pharmaceutically acceptable salt thereof and BCMA-directed therapy (e.g., belantamab mafodotin). In some aspects, the patient with ovarian cancer exhibits a stringent complete response following administration of the nirogacestat or pharmaceutically acceptable salt thereof (e.g., a dihydrobromide salt form) and BCMA-directed therapy (e.g., belantamab mafodotin). In some aspects, the patient with ovarian cancer exhibits a minor response following administration of the nirogacestat or pharmaceutically acceptable salt thereof (e.g., a dihydrobromide salt form) and BCMA-directed therapy (e.g., belantamab mafodotin). In some aspects, the patient with ovarian cancer exhibits a partial response following administration of the nirogacestat or pharmaceutically acceptable salt thereof (e.g., a dihydrobromide salt form) and BCMA-directed therapy (e.g., belantamab mafodotin). In some aspects, the patient with ovarian cancer exhibits a very good partial response following administration of the nirogacestat or pharmaceutically acceptable salt thereof (e.g., a dihydrobromide salt form) and BCMA-directed therapy (e.g., belantamab mafodotin). In some aspects, the patient with ovarian cancer exhibits stable disease following administration of the nirogacestat or pharmaceutically acceptable salt thereof (e.g., a dihydrobromide salt form) and BCMA-directed therapy (e.g., belantamab mafodotin).

EXAMPLES

Example 1: Pharmacokinetics

The pharmacokinetic parameters for single oral doses of nirogacestat dihydrobromide (PF-03084014) are provided in Tables 2A-2D below.

TABLE 2A

| COHORT 1: 150 mg (3 × 50 mg) Period 1 | | | | | | | |
|---|---|---|---|---|---|---|---|
| Statistic | | N | Min | Median | Max | Geometric Mean | Geometric CV % |
| Half-life | (h) | 10 | 18.1 | 26.3 | 32.0 | 25.0 | 18.6 |
| $T_{max}$ | (h) | 10 | 1.00 | 1.49 | 2.00 | 1.34 | 23.8 |
| $C_{max}$ | (ng/mL) | 10 | 547 | 697 | 1120 | 733 | 25.2 |
| $AUC_{last}$ | (h*ng/ml) | 10 | 2080 | 2580 | 4660 | 2960 | 33.0 |
| $AUC_{inf}$ | (h*ng/ml) | 10 | 2160 | 2640 | 4870 | 3050 | 33.4 |
| Vz/F | (L) | 10 | 1060 | 1830 | 3210 | 1770 | 38.5 |
| CL/F | (L/h) | 10 | 30.8 | 57.0 | 69.5 | 49.2 | 33.4 |

TABLE 2B

| COHORT 1: 150 mg (1 × 150 mg) Period 2 | | | | | | | |
|---|---|---|---|---|---|---|---|
| Statistic | | N | Min | Median | Max | Geometric Mean | Geometric CV % |
| Half-life | (h) | 10 | 13.3 | 26.3 | 34.7 | 24.7 | 28.1 |
| $T_{max}$ | (h) | 10 | 0.500 | 1.50 | 1.52 | 1.20 | 37.2 |
| $C_{max}$ | (ng/mL) | 10 | 456 | 662 | 1200 | 686 | 30.5 |
| $AUC_{last}$ | (h*ng/ml) | 10 | 1790 | 3040 | 5720 | 2930 | 34.5 |
| $AUC_{inf}$ | (h*ng/ml) | 10 | 1830 | 3100 | 5880 | 3020 | 34.3 |
| Vz/F | (L) | 10 | 864 | 1720 | 3090 | 1770 | 49.2 |
| CL/F | (L/h) | 10 | 25.5 | 48.4 | 82.0 | 49.7 | 34.3 |

TABLE 2C

| COHORT 2: 100 mg Period 1 | | | | | | | |
|---|---|---|---|---|---|---|---|
| Statistic | | N | Min | Median | Max | Geometric Mean | Geometric CV % |
| Half-life | (h) | 8 | 19.7 | 24.4 | 34.6 | 25.2 | 21.6 |
| $T_{max}$ | (h) | 8 | 0.500 | 1.28 | 2.00 | 1.19 | 44.6 |
| $C_{max}$ | (ng/ml) | 8 | 259 | 433 | 654 | 435 | 33.2 |
| $AUC_{last}$ | (h*ng/ml) | 8 | 777 | 1660 | 3710 | 1720 | 52.0 |
| $AUC_{inf}$ | (h*ng/ml) | 8 | 805 | 1710 | 3940 | 1780 | 52.4 |
| Vz/F | (L) | 8 | 1000 | 2040 | 3880 | 2040 | 51.7 |
| CL/F | (L/h) | 8 | 25.4 | 58.4 | 124 | 56.1 | 52.4 |

TABLE 2D

| COHORT 3: 50 mg Period 1 | | | | | | | |
|---|---|---|---|---|---|---|---|
| Statistic | | N | Min | Median | Max | Geometric Mean | Geometric CV % |
| Half-life | (h) | 8 | 4.24 | 23.3 | 32.8 | 19.3 | 73 |
| $T_{max}$ | (h) | 8 | 0.5 | 1 | 1.52 | 0.829 | 43.4 |
| $C_{max}$ | (ng/mL) | 8 | 49.6 | 209 | 507 | 183 | 82.9 |
| $AUC_{last}$ | (h*ng/mL) | 8 | 71.6 | 653 | 2120 | 545 | 140 |
| $AUC_{inf}$ | (h*ng/mL) | 8 | 75.7 | 674 | 2140 | 571 | 137.36 |
| Vz/F | (L) | 8 | 677 | 2730 | 5060 | 2440 | 67.3 |
| CL/F | (L/h) | 8 | 23.4 | 74.9 | 660 | 87.6 | 137 |

The pharmacokinetic parameters for oral doses of 150 mg (free base equivalent dose) nirogacestat dihydrobromide twice daily at steady state exposure is provided in Table 2E below.

TABLE 2E

| Pharmacokinetics for 150 mg (free base equivalent dose) nirogacestat dihydrobromide twice daily at steady state exposure (% CV) | |
|---|---|
| $C_{max}$ (% CV) | 1246 (79) ng/ml |
| $AUC_{tau}$ (% CV) | 6430 (89) ng · h/mL |
| Time to steady-state | Approximately 8 days |

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations following, in general, the principles and including such departures from the present disclosure that come within known or customary practice within the art to which the invention pertains and can be applied to the essential features hereinbefore set forth, and follows in the scope of the claimed.

What is claimed:

1. A method for therapeutic treatment of ovarian cancer in a patient in need thereof comprising orally administering to the patient 150 mg (free base equivalent dose) of nirogacestat or a pharmaceutically acceptable salt thereof twice daily, wherein the patient has refractory or recurrent disease after previous treatment, and the method further comprises one or more of:

(a) upon the patient having Grade 3 or 4 diarrhea persisting for at least 3 days despite medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily;

(b) upon the patient having Grade 3 or 4 hypophosphatemia persisting for at least 3 days despite replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily;

(c) upon the patient having Grade 3 or 4 hypokalemia despite replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily;

(d) upon the patient having an alanine transaminase (ALT) or aspartate aminotransferase (AST) of 3 to 5 times upper limit of normal (ULN), withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily; and (e) upon the patient having an ALT or AST of greater than 5 times ULN, permanently discontinuing treatment with the nirogacestat or pharmaceutically acceptable salt thereof, wherein the nirogacestat or pharmaceutically acceptable salt thereof is nirogacestat dihydrobromide.

2. The method of claim 1, further comprising:

(f) for another severe adverse reaction, life-threatening adverse reaction, or persistent intolerable Grade 2 adverse event, withholding the nirogacestat or pharmaceutically acceptable salt thereof until the adverse reaction is resolved to no higher than a Grade 1 adverse reaction or baseline and then, after considering the potential benefit and likelihood of recurrence of the adverse reaction, (A) restarting oral administration of the nirogacestat or pharmaceutically acceptable salt thereof at a dose of 100 mg (free base equivalent dose) twice daily and (B) upon recurrence of the severe or life-threatening adverse reaction at the 100 mg (free base equivalent dose) twice daily dose, permanently discontinuing treatment with the nirogacestat or pharmaceutically acceptable salt thereof.

3. The method of claim 1, wherein the method comprises (a) upon the patient having Grade 3 or 4 diarrhea persisting for at least 3 days despite medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily.

4. The method of claim 1, wherein the method comprises (b) upon the patient having Grade 3 or 4 hypophosphatemia persisting for at least 3 days despite replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily.

5. The method of claim 1, wherein the method comprises (c) upon the patient having Grade 3 or 4 hypokalemia despite replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily.

6. The method of claim 1, wherein the method comprises (d) upon the patient having an ALT or AST of 3 to 5 times ULN, withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily.

7. The method of claim 1, wherein the method comprises (e) upon the patient having an ALT or AST of greater than 5 times ULN, permanently discontinuing treatment with the nirogacestat or pharmaceutically acceptable salt thereof.

8. The method of claim 1, wherein the method comprises:

(a) upon the patient having Grade 3 or 4 diarrhea persisting for at least 3 days despite medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily;

(b) upon the patient having Grade 3 or 4 hypophosphatemia persisting for at least 3 days despite replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily;

(c) upon the patient having Grade 3 or 4 hypokalemia despite replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily;

(d) upon the patient having an ALT or AST of 3 to 5 times ULN, withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily; and (e) upon the patient having an ALT or AST of greater than 5 times ULN, permanently discontinuing treatment with the nirogacestat or pharmaceutically acceptable salt thereof.

9. The method of claim 1, wherein the method comprises:

(a) upon the patient having Grade 3 or 4 diarrhea persisting for at least 3 days despite medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily;

(b) upon the patient having Grade 3 or 4 hypophosphatemia persisting for at least 3 days despite replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily;

(c) upon the patient having Grade 3 or 4 hypokalemia despite replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily;

(d) upon the patient having an ALT or AST of 3 to 5 times ULN, withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily;

(e) upon the patient having an ALT or AST of greater than 5 times ULN, permanently discontinuing treatment with the nirogacestat or pharmaceutically acceptable salt thereof; and (f) for another severe adverse reaction, life-threatening adverse reaction, or persistent intolerable Grade 2 adverse event, withholding the nirogacestat or pharmaceutically acceptable salt thereof until the adverse reaction is resolved to no higher than a Grade 1 adverse reaction or baseline and then, after considering the potential benefit and likelihood of recurrence of the adverse reaction, (A) restarting oral administration of the nirogacestat or pharmaceutically acceptable salt thereof at a dose of 100 mg (free base equivalent dose) twice daily and (B) upon recurrence of the severe or life-threatening adverse reaction at the 100 mg (free base equivalent dose) twice daily dose, permanently discontinuing treatment with the nirogacestat or pharmaceutically acceptable salt thereof.

10. The method of claim 1, wherein upon the patient having a Grade 3 dermatologic reaction, withholding the nirogacestat or pharmaceutically acceptable salt thereof until the dermatologic reaction is resolved to no higher than a Grade 1 dermatologic reaction and then restarting oral administration of the nirogacestat or pharmaceutically acceptable salt thereof at a dose of 100 mg (free base equivalent dose) twice daily.

11. The method of claim 1, wherein the patient has a mutation in the adenomatous polyposis coli (APC) tumor suppressor gene.

12. The method of claim 1, wherein the patient has a mutation in the CTNNB1 (β-catenin) gene.

13. The method of claim 1, wherein the patient was previously treated with a tyrosine kinase inhibitor.

14. The method of claim 1, wherein the patient is an adult.

15. The method of claim 1, wherein the patient is a postmenopausal woman.

16. The method of claim 1, wherein gastric acid reducing agents are avoided or administered 4 hours after administration of the nirogacestat or pharmaceutically acceptable salt thereof.

17. A method for therapeutic treatment of ovarian cancer in a treatment naïve patient comprising orally administering to the patient 150 mg (free base equivalent dose) of nirogacestat or a pharmaceutically acceptable salt thereof twice daily, wherein the ovarian cancer is an ovarian granulosa cell tumor (OvGCT).

18. The method of claim 1, wherein the patient, after initial administration of 150 mg (free base equivalent dose) of nirogacestat or a pharmaceutically acceptable salt thereof, exhibits a $C_{max}$ of nirogacestat of from about 480 to about 950 ng/ml.

19. The method of claim 1, wherein the patient, after initial administration of 150 mg (free base equivalent dose) of nirogacestat or a pharmaceutically acceptable salt thereof, exhibits a $C_{max}$ of nirogacestat of from about 550 to about 1100 ng/ml.

20. The method of claim 19, wherein the patient, after initial administration of 150 mg (free base equivalent dose) of nirogacestat or a pharmaceutically acceptable salt thereof, exhibits a $C_{max}$ of nirogacestat of from about 600 to about 800 ng/mL.

21. The method of claim 1, wherein the patient, after initial administration of 150 mg (free base equivalent dose) of nirogacestat or a pharmaceutically acceptable salt thereof, exhibits an $AUC_{last}$ of nirogacestat of less than 4000 ng·h/mL.

22. The method of claim 1, wherein the patient, after initial administration of 150 mg (free base equivalent dose) of nirogacestat or a pharmaceutically acceptable salt thereof, exhibits an $AUC_{last}$ of nirogacestat of from about 2000 to about 4000 ng·h/mL.

23. The method of claim 1, wherein the patient, after initial administration of 150 mg (free base equivalent dose) of nirogacestat or a pharmaceutically acceptable salt thereof, exhibits an $AUC_{inf}$ of nirogacestat of from about 2200 to about 4800 ng·h/mL.

24. The method of claim 23, wherein the patient, after initial administration of 150 mg (free base equivalent dose) of nirogacestat or a pharmaceutically acceptable salt thereof, exhibits an $AUC_{inf}$ of nirogacestat of from about 2200 to about 3300 ng·h/mL.

25. The method of claim 1, wherein the patient exhibits, at steady state exposure from administration of 150 mg (free base equivalent dose) of nirogacestat or a pharmaceutically acceptable salt thereof twice daily, a $C_{max}$ of nirogacestat of from about 300 to 700 ng/mL.

26. The method of claim 25, wherein the patient exhibits, at steady state exposure from administration of 150 mg (free base equivalent dose) of nirogacestat or a pharmaceutically acceptable salt thereof twice daily, a $C_{max}$ of nirogacestat of from about 400 to about 600 ng/mL.

27. The method of claim 1, wherein the patient exhibits, at steady state exposure from administration of 150 mg (free base equivalent dose) of nirogacestat or a pharmaceutically acceptable salt thereof twice daily, an $AUC_{tau}$ of nirogacestat of from about 2200 to about 4800 ng·h/mL.

28. The method of claim 27, wherein the patient exhibits, at steady state exposure from administration of 150 mg (free base equivalent dose) of nirogacestat or a pharmaceutically acceptable salt thereof twice daily, an $AUC_{tau}$ of nirogacestat of from about 3000 to about 3700 ng·h/mL.

29. A method for therapeutic treatment of ovarian cancer in a patient in need thereof comprising orally administering to the patient 150 mg (free base equivalent dose) of nirogacestat or a pharmaceutically acceptable salt thereof twice daily, wherein the patient has refractory or recurrent disease after previous treatment, and the method further comprises one or more of:

(a) upon the patient having Grade 3 or 4 diarrhea persisting for at least 3 days despite medical therapy, withholding the nirogacestat or pharmaceutically acceptable salt thereof until the diarrhea is resolved to no higher than a Grade 1 diarrhea or baseline and then restarting oral administration of the nirogacestat or pharmaceutically acceptable salt thereof at a dose of 100 mg (free base equivalent dose) twice daily:

(b) upon the patient having Grade 3 or 4 hypophosphatemia persisting for at least 3 days despite replacement therapy, withholding the nirogacestat or pharmaceutically acceptable salt thereof until the hypophosphatemia is resolved to no higher than a Grade 1 hypophosphatemia or baseline and then restarting oral administration of the nirogacestat or pharmaceutically acceptable salt thereof at a dose of 100 mg (free base equivalent dose) twice daily:

(c) upon the patient having Grade 3 or 4 hypokalemia despite replacement therapy, withholding the nirogacestat or pharmaceutically acceptable salt thereof until the hypokalemia is resolved to no higher than a Grade 1 hypokalemia or baseline and then restarting oral administration of the nirogacestat or pharmaceutically acceptable salt thereof at a dose of 100 mg (free base equivalent dose) twice daily;

(d) upon the patient having an alanine transaminase (ALT) or aspartate aminotransferase (AST) of 3 to 5 times upper limit of normal (ULN), withholding the nirogacestat or pharmaceutically acceptable salt thereof until the ALT, AST, or both are resolved to less than 3 times ULN or baseline and then restarting oral administration of the nirogacestat or pharmaceutically acceptable salt thereof at a dose of 100 mg (free base equivalent dose) twice daily; and (e) upon the patient having an ALT or AST of greater than 5 times ULN, permanently discontinuing treatment with the nirogacestat or pharmaceutically acceptable salt thereof, wherein the ovarian cancer is an ovarian granulosa cell tumor (OvGCT).

30. The method of claim 1, wherein the patient exhibits hyperestrogenism.

* * * * *